US009169331B2

(12) United States Patent
Liu et al.

(10) Patent No.: US 9,169,331 B2
(45) Date of Patent: Oct. 27, 2015

(54) SEPARATION OF GLYCANS BY MIXED-MODE LIQUID CHROMATOGRAPHY

(71) Applicant: DIONEX CORPORATION, Sunnyvale, CA (US)

(72) Inventors: Xiaodong Liu, Cupertino, CA (US); Udayanath Aich, Sunnyvale, CA (US); Christopher A. Pohl, Union City, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 127 days.

(21) Appl. No.: 13/724,178

(22) Filed: Dec. 21, 2012

(65) Prior Publication Data

US 2014/0178912 A1   Jun. 26, 2014

(51) Int. Cl.
  *C12Q 1/28* (2006.01)
  *C08B 37/00* (2006.01)
  *B01D 15/38* (2006.01)
  *C07K 1/16* (2006.01)
  *B01J 41/20* (2006.01)
  *B01J 43/00* (2006.01)
  *B01J 20/281* (2006.01)

(52) U.S. Cl.
  CPC ........ *C08B 37/0063* (2013.01); *B01D 15/3847* (2013.01); *B01J 41/20* (2013.01); *B01J 43/00* (2013.01); *C07K 1/165* (2013.01); *G01N 30/482* (2013.01)

(58) Field of Classification Search
  CPC .. B01D 15/3847; B01D 41/20; B01D 15/363; B01D 15/305; B01D 15/325; C07K 1/165; C08B 37/0063; B01J 43/00
  See application file for complete search history.

(56) References Cited

U.S. PATENT DOCUMENTS

| | | | |
|---|---|---|---|
| 3,341,564 A * | 9/1967 | Potts et al. ............. 558/18 |
| 3,506,642 A * | 4/1970 | Koh et al. ............. 536/51 |
| 4,101,460 A | 7/1978 | Small et al. | |
| 4,119,580 A | 10/1978 | Smith, Jr. et al. | |
| 4,351,909 A | 9/1982 | Stevens et al. | |
| 4,376,047 A | 3/1983 | Pohl | |
| 4,382,124 A | 5/1983 | Meitzner et al. | |
| 4,383,047 A | 5/1983 | Stevens et al. | |
| 4,519,905 A | 5/1985 | Stevens et al. | |
| 4,833,083 A | 5/1989 | Saxena | |
| 4,927,539 A | 5/1990 | Stevens et al. | |
| 5,024,767 A | 6/1991 | Kubo et al. | |
| 5,030,352 A | 7/1991 | Varady et al. | |
| 5,130,343 A | 7/1992 | Frechet et al. | |
| 5,260,094 A | 11/1993 | Giannelis et al. | |
| 5,324,752 A | 6/1994 | Barretto et al. | |
| 5,334,310 A | 8/1994 | Frechet et al. | |
| 5,431,807 A | 7/1995 | Frechet et al. | |
| 5,453,185 A | 9/1995 | Frechet et al. | |
| 5,532,279 A | 7/1996 | Barretto et al. | |
| 5,597,489 A | 1/1997 | Schneider et al. | |
| 5,728,457 A | 3/1998 | Frechet et al. | |
| 5,865,994 A | 2/1999 | Riviello | |
| 5,925,253 A | 7/1999 | Pohl et al. | |
| 5,929,214 A | 7/1999 | Peters et al. | |
| 5,936,003 A | 8/1999 | Pohl et al. | |
| 5,968,363 A | 10/1999 | Riviello et al. | |
| 6,045,842 A | 4/2000 | Mozaffar et al. | |
| 6,096,870 A | 8/2000 | Mozaffar et al. | |
| 6,248,798 B1 | 6/2001 | Slingsby et al. | |
| 6,528,167 B2 | 3/2003 | O'Gara | |
| 6,544,484 B1 | 4/2003 | Kaufman et al. | |
| 6,568,245 B2 | 5/2003 | Kaufman | |
| 6,887,384 B1 | 5/2005 | Frechet et al. | |
| 6,987,183 B2 | 1/2006 | Heikkila et al. | |
| 7,074,331 B2 | 7/2006 | Allington et al. | |
| 7,303,671 B2 | 12/2007 | Srinivasan et al. | |
| 7,767,462 B2 | 8/2010 | Liu et al. | |
| 7,811,453 B2 | 10/2010 | Yotani et al. | |
| 7,847,936 B2 | 12/2010 | Jarrell | |
| 7,911,609 B2 | 3/2011 | Jarrell | |
| 8,089,627 B2 | 1/2012 | Jarrell | |
| 8,182,679 B2 | 5/2012 | Liu et al. | |
| 8,246,832 B2 | 8/2012 | Lomas et al. | |
| 8,304,250 B2 | 11/2012 | Parsons et al. | |
| 8,497,358 B2 | 7/2013 | Suenaga et al. | |

(Continued)

FOREIGN PATENT DOCUMENTS

CN     102179238 A    9/2011
EP     0462795 A2     12/1991

(Continued)

OTHER PUBLICATIONS

Takegawa et al. Analytical Chemistry (2005) 77(7): 2097-2106.*
Tosho Bioscience website for TSKgel Amide 80 columns http://www.separations.eu.tosohbioscience.com/Products/HPLCColumns/ByMode/NormalHydrophilic/TSKgel+Amide-80.htm downloaded Jan. 11, 2015.*
tosho bioscience website for TSKgel DEAE-5PW http://www.separations.us.tosohbioscience.com/ProductsPrinterFriendlyTemplate.aspx?NRMODE=Published&NRORIGINALURL=%2fProducts%2fProcessMedia%2fByMode%2flEC%2fTSKgelDEAE5PW.htm&NRNODEGUID=%7b3C4473BA-D8D8-4EA4-8DD4-1B264D5915E2%7d&NRCACHEHINT=Guest downloaded Jan. 11, 2015.*
Tosho bioscience Website for TSKgel http://www.tskgel.com/ downloaded Jan. 11, 2015.*
Hykollari et al. J. Proteome Research (2013) 12: 1173-1187.*
Thermo Fisher Scientific Inc. (2015) IonPac AS11 Anion-Exchange Column Specifications. www.thermoscientific.com/dionex.*
Anumula, "High-Sensitivity and High-Resolution Methods for Glycoprotein Analysis," Anal. Biochem. 283, 17-26 (2000).
Ruhaak et al., "Glycan Labeling Strategies and Their Use in Identification and Quantification," Anal. Bioanal. Chem. 397, 3457-3481 (2010).

(Continued)

*Primary Examiner* — Susan Hanley
(74) *Attorney, Agent, or Firm* — Jeffry S. Mann

(57) ABSTRACT

An exemplary multimodal chromatographic medium of the invention includes one or more strong anion exchange, weak anion exchange, strong cation exchange and/or weak cation exchange binding sites in combination with one or more reverse phase and/or hydrophilic interaction chromatography binding site. In an exemplary embodiment, the sites interact with one or more glycans in a mixture of glycans in a manner that allows separation of glycans in the mixture and analysis of the glycan mixture. The media are incorporated into devices and systems for chromatographic analysis. Also provided are methods of using the multimodal media of the invention to analyze glycans.

41 Claims, 13 Drawing Sheets

(56) References Cited

U.S. PATENT DOCUMENTS

| | | | |
|---|---|---|---|
| 2004/0147033 | A1 | 7/2004 | Shriver et al. |
| 2005/0064192 | A1 | 3/2005 | Jiang et al. |
| 2005/0092910 | A1 | 5/2005 | Geromanos et al. |
| 2005/0161399 | A1 | 7/2005 | Dillon et al. |
| 2006/0054559 | A1 | 3/2006 | Liu et al. |
| 2006/0070937 | A1 | 4/2006 | Rustamov et al. |
| 2007/0062854 | A1 | 3/2007 | Pohl et al. |
| 2008/0118932 | A1 | 5/2008 | Toler et al. |
| 2008/0164211 | A1 | 7/2008 | Lindner et al. |
| 2008/0207487 | A1 | 8/2008 | DeFrees et al. |
| 2008/0219952 | A1 | 9/2008 | Fischer et al. |
| 2009/0277838 | A1 | 11/2009 | Liu et al. |
| 2009/0324617 | A1 | 12/2009 | Satomaa et al. |
| 2010/0075375 | A1 | 3/2010 | Defrees et al. |
| 2010/0320149 | A1 | 12/2010 | Axen et al. |
| 2011/0117601 | A1 | 5/2011 | Haberger et al. |
| 2011/0284465 | A1 | 11/2011 | Liu et al. |
| 2012/0302516 | A1* | 11/2012 | Nantz et al. ............ 514/34 |
| 2012/0308549 | A1 | 12/2012 | Fogh et al. |

FOREIGN PATENT DOCUMENTS

| | | |
|---|---|---|
| GB | 2194900 A2 | 3/1988 |
| WO | 03022433 A2 | 3/2003 |
| WO | 2005047886 A1 | 5/2005 |
| WO | 2006088760 A1 | 8/2006 |
| WO | 2008128225 A1 | 10/2008 |
| WO | WO 2009027041 A1 * | 3/2009 |
| WO | 2009137275 A1 | 11/2009 |
| WO | 2010068272 A1 | 6/2010 |

OTHER PUBLICATIONS

Neville et al., "Development of a Single Column Method for the Separation of Lipid- and Protein-Derviced Oligosaccharides," J. of Proteome Res., 8, 681-687 (2009).

Spearman et al., "The Role of Glysosylation in Therapeutic Antibodies," Chapter 12, M. Al-Rubeai (ed.) Antibody Expression and Production, Cell Engineering 7, BOI 10.1007/978-94-007-1257-7_12, copyright Springer Science +Business Media V.V. 2011.

Tousi et al., "Technologies and Strategies for Glycoproteomics and Glycomics and Their Application to Clinical Biomarker Research," Anal. Methods, 3 20-32 (2011).

Takegawa et al., "Separation of Isomeric 2-aminopyridine Derivatized N-glycans and N-glycopeptides of Human Serium Immunoglobulin G by Using a Zwitterionic Type of Hydrophilic-interaction Chromatography," J. of Chromatography A,m 1113, 177-181 (2006).

Yamada et al., Recent Advances in the Analysis of Carbohydrates for Biomedical Use, J. of Pharm. and Biomed. Anal., 55, 702-727 (2011).

Thermo Scientific/Dionex Datasheet: Acclaim HILIC-10 Column for Separating Highly Hydrophilic Molecules, 6 pages, 2010.

Thermo Scientific/Dionex Datasheet: The Acclaim Mixed-Mode HILIC-1 Column, a Powerful Tool for Separating Polar Molecules, 6 pages, 2007.

Thermo Scientific/Dionex Datasheet: Acclaim Mixed-Mode WAX-1 Column, Total Control of Selectivity, 8 pages, 2007.

Takegawa et al., "Simple separation of isomeric sialylated N-glycopeptides by a zwitterionic type of hydrophilic interaction chromatography," J Sep Sci (2006) 29:2533-2540.

Pinkerton, T. C., "High-performance liquid chromatography packing materials for the analysis of small molecules in biological matrices by direct injection," J. Chromatogr., 544, (1991) 13.

Haginaka, J., "Drug determination in serum by liquid chromatography with restricted access stationary phases," Trends Anal Chem., 10, (1991) 17.

Berge et al., "Pharmaceutical salts," Journal of Pharmaceutical Science 1977, 66: 1-19.

Ikada et al., "Reaction of Poly(vinyl Alcohol) with Potassium Persulfate and Graft Copolymerization," Journal of Polymer Science, vol. 12, 1829-1839 (1974).

Merck Datasheet: SeQuant, A practical guide to HILIC including ZIC-HILIC applications, copyright 2005-2008, 30 pages.

Maehr, "A Proposed New Convention for Graphic Presentation of Molecular Geometry and Topography," J. Chem. Ed., 62, 114-120 (1985).

Minakuchi, et al., "Octadecylsilylated Porous Silica Rods as Separation Media for Reversed-Phase Liquid Chromatography," Anal. Chem., 68, 3498-3501, 1996.

Minackuchi et al., "Effect of Domain Size on the Performance of Octadecylsilylated Continuous Porous Silica Columns in Reversed-Phase Liquid Chromatography," J. Chromatogr., 797, 121-131, 1998.

Hutchinson, et al., "Preparation and Characterisation of Anion-Exchange Latex-Coated Silica Monoliths for Capillary Electrochromatography," J. Chromatogr., 1109, 10-18, 2006.

Glenn et al., "Ion Chromatography on a Latex-Coated Silica Monolith Column," J. Chromatogr., 1155, 8-14, 2007.

Majors, "Developments in HPLC Column Packing Design," LCGC LC Column Technology Supplement, Apr. 8-15, 2006.

Majors, "Developments in HPLC Column Technology (2006-2008)," LCGC LC Column Technology Supplement, Apr. 10-17, 2008.

Majors, New Chromatography Columns and Accessories at Pittcon 2008: Part I, LCGC North America, vol. 26, No. 3, pp. 238-254, Mar. 2008.

Kalay et al., "Online nanoliquid chromatography-mass spectrometry and nanofluorescence detection for high-resolution quantitative N-glycan analysis," Anal. Biochem. 423, 153-162, 2012.

Kallberg et al., "Application of a pH responsive multimodal hydrophobic interaction chromatography medium for the analysis of glycosylated proteins," J Chromatography A, 1218(5), 678-683, 2011.

Townsend et al., "Multimode High-Performance Liquid Chromatography of Fluorescently Labeled Oligosaccharides from Glycoproteins," Anal. Biochem. 239, 200-207, 1996.

Liu et al., "Chromatographic evaluation of reversed-phase/anion-exchange-cation-exchange trimodal stationary phases prepared by electrostatically driven self-assembly process," J of Chromatography, 1218(22), 3407-3412, 2011.

Shen et al., "Preparation and chromatographic evaluation of a cysteine-bonded zwitterionic hydrophilic interaction liquid chromatography stationary phase," J of Chromatogr A, 1228, 175-182, 2012.

Strege et al., "Mixed-mode anion-cation exchange/hydrophilic interaction liquid chromatography-electrospray mass spectrometry as an alternative to reversed phase for small molecule drug discovery," Anal Chem, 72(19), 4629-4633, 2000.

Deguchi et al., "Two-dimensional hydrophilic interaction chromatography coupling anion-exchange and hydrophilic interaction columns for separation of 2-pyridylamino derivatives of neutral and sialylated N-glycans," 1189(1-2), 169-74, 2008.

Gohlke et al., "Separation of N-glycans by HPLC," Methods Mol Biol, 446, 239-54, 2008.

Ibrahim et al., "Agglomerated Silica Monolithic Column for Hydrophilic Interaction LC," Journal of Separation Science, vol. 33:6-7, 773-778, 2010.

Kalay et al., "Enhanced glycan nanoprofiling by weak anion exchange preparative chromatography, mild acid desialylation, and nanoliquid chromatography-mass spectrometry with nanofluorescence detection," Electrophoresis, 34(16) 2350-6, 2013.

Kazarian et al., "Ion-exchange and hydrophobic interactions affecting selectivity for neutral and charged solutes on three structurally similar agglomerated ion-exchange and mixed-mode station phases," Analytica Chemica Acta, 803, pp. 143-153, 2013.

Lammerhofer et al., "Mixed-mode ion-exchangers and their comparative chromatographic characterization in reversed-phase and hydrophilic interaction chromatography elution modes," J. Separation Science, 31(14), 2572-88, 2008.

Liu et al., "HILIC Behavior of a Reversed-Phase/Cation Exchange/Anion Exchange Trimode Column," Journal of Separation Science, vol. 33: 6-7, 779-786, 2010.

Nogueira et al., "Alternative high-performance liquid chromatographic peptide separation and purification concept using a new mixed-mode reversed-phase/weak anion-exchange type stationary phase," J of Chromatography A, 1089 (1-2) 158-69, 2005.

(56) References Cited

OTHER PUBLICATIONS

Nogueira et al., "Silica-based monolithic columns with mixed-mode reversed-phase/weak anion-exchange selectivity principle for high-performance liquid chromatography," J Separation Science, 29(7), 966-78, 2006.

Rudd et al., "A high-performance liquid chromatography based strategy for rapid, sensitive sequencing of N-linked oligosaccharide modifications to proteins in sodium dodecyl sulphate polyacrylamide electrophoresis gel bands," Proteomics, 1(2), 285-94, 2001.

Wuhrer et al., "Two-dimensional HPLC separation with reverse-phase-nano-LC-MS/MS for the characterization of glycan pools after labeling with 2-aminobenzamide," Methods Mol Biol, 534, 79-91, 2009.

Yuen et al., "High-performance liquid chromatographic profiling of fluorescent labelled N-glycans on glycoproteins," 16 (4), 247-54, 2002.

Pohl et al., U.S. Appl. No. 11/753,934, filed May 25, 2007 (spec, claims, abstract, drawings only).

* cited by examiner

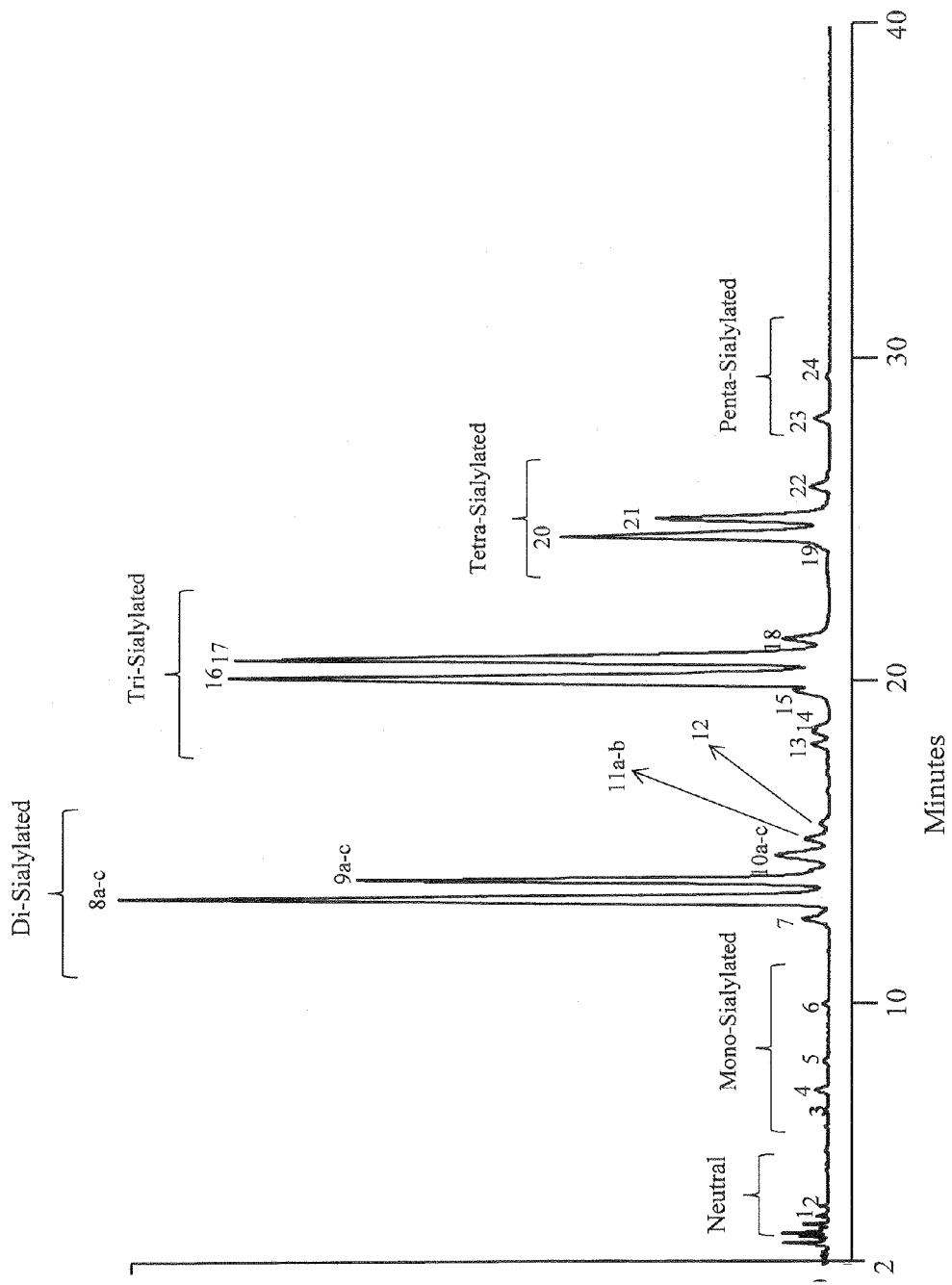

SEPARATION OF GLYCANS BY MIXED-MODE LIQUID CHROMATOGRAPHY

BACKGROUND OF THE INVENTION

Glycans are widely distributed in biological systems in the free state as well as conjugated forms as parts of glycoproteins, glycolipids, and proteoglycans. They are involved in a wide range of biological and physiological processes including recognition, regulatory functions, cellular communication, gene expression, stability and activity of proteins therapeutics, cellular immunity, growth and development. Biological and physiological functions of glycans are often dependent on the structure and types of oligosaccharides attached to the proteins or lipids. The structures of glycans are quite diverse and complex due to post-translational modifications and physiological conditions. Thus, it is highly challenging to analyze comprehensive glycan profiles (i.e. glycome) and determine the structure of glycans for clinical use HPAEC-PAD (High Performance Anion Exchange Chromatography with Pulsed Amperometric Detection) was the first routine assay method developed for glycan analysis. This ion chromatography (IC) method can separate carbohydrates via specific interactions between the hydroxyl groups of glycans and chromatographic medium at high pH. The glycans are chromatographed as anionic species and interact with the column based on glycan charge, size, composition, isomers and linkage(s). This analytical method provides a profile of the overall glycosylation or oligosaccharide population present on a product, or at a specific glycosylation site, which can be used for batch comparison studies. However, a significant disadvantage of HPAEC-PAD separation of glycans is the need to use a relatively high salt concentration. In such a case, a desalter column is often used so that the mobile phase is compatible with mass spectrometry.

Various modes of HPLC separation have been developed for the analysis of glycans, including normal phase or hydrophilic interaction (HILIC), ion-exchange and reversed-phase. Because glycans are highly hydrophilic and polar substances, HILIC is extensively used for glycan analysis. The separation columns are typically amide, amine or zwitterionic-based packing materials. The amide HILIC column separates glycans mainly by hydrogen bonding, resulting in size and composition based separation. However, no charge based separation can be achieved with this approach. Both amine-based and zwitterionic columns show ionic interactions with charged glycans (native or labeled) and, although they separate glycans based on charge, they provide relatively low resolution between glycans of the same charge (e.g., polarity and/or magnitude of charge). In addition, the inherently strong ionic interactions between multiply charged glycans and the stationary phase often requires a high eluent buffer concentration, adversely affecting MS sensitivity.

A few reports have described the use of amino or quaternized amine columns as anion-exchange/HILIC mixed-mode columns for glycan analysis (Ruhaak et al., Anal. Bioanal Chem (2010) 397:3457-3481; Anumula et al., Anal Biochem (2000) 283:17-26; and Neville et al., J Proteome Res (2009) 8:681-687). However, the amino or quaternized amine columns referenced above have only one mode, which is an ion exchange mode, and thus, are not mixed mode. In addition, these columns have only one type of chromatographic functional group, which in this case is either an amino or quaternized amine. The above references do not describe separation conditions over a pH range where the amino group would have a neutral charge (i.e., unprotonated). Note that a quaternized amine cannot have a neutral charge even at high pH. A protonated amine group will act as anion exchange group and not as a HILIC group. It should be noted that although increasing retention times with increasing solvent concentration provides evidence of a HILIC interaction, it also provides evidence of other retention modes such as ion exchange and the interaction of salts with zwitterionic modes. As such, increasing retention times with increasing solvent concentration does not by itself indicate a HILIC interaction. Amino and quaternized amine columns suffer from the disadvantages of having a long retention time (e.g., >60 minutes) and requiring relatively high salt concentrations. In general, relatively high salt concentrations interfere with the detection of glycans with mass spectrometry.

Reports have described the use of zwitterionic sulfobetaine columns as a zwitterionic ion chromatography (ZIC)/HILIC mixed-mode columns for glycan analysis (Ruhaak et al., Anal. Bioanal Chem (2010) 397:3457-3481; Takegawa et al., Journal of Chromatography A, (2006) 1113:177-181; and Takegawa et al., J Sep Sci (2006) 29:2533-2540). However, the zwitterionic columns referenced above have only one mode, which is a zwitterionic mode based on the sulfobetaine stationary phase, and thus, are not mixed mode. In addition, these columns have only one type of chromatographic functional group, which in this case is a zwitterionic sulfobetaine group. Such sulfobetaine groups are net neutral over a very broad pH range, interacting via an electrostatic mechanism with salts in an ionic strength dependant manner, which is different than an uncharged HILIC mechanism. It should be noted that although increasing retention times with increasing solvent concentration provides evidence of a HILIC interaction, it also is indicative of other retention modes such as ion exchange and the interaction of salts with zwitterionic modes. As such, increasing retention times with increasing solvent concentration does not by itself indicate a HILIC interaction. The zwitterionic phase column suffers from the disadvantage of showing relatively poor resolution for a group of glycans having the same charge.

It is generally very desirable to detect and characterize glycan analytes in the eluate by using mass spectrometry, however, the art clearly teaches that operating under conditions in which the anion-exchange phase is highly ionized is unacceptable when combined with mass spectroscopic detection. The zwitterionic mode operates via a salt exchange retention mechanism, which is inherently less selective than ion exchange. High solvent concentrations simply increase the strength of the salt exchange interactions.

Applicant believes that there is a need for new multimodal chromatographic media and methods of analyzing glycans using these media that would ideally provide high resolution between different glycans, unique selectivity based on size, composition, structure (e.g., isomerism, linkages), and/or charge. Further, Applicant also believes that if the glycans eluted from the media could be detected by standard methodology (e.g., mass spectrometry, fluorescence detection) with no, or minimal, clean up or purification post-analysis and pre-detection (e.g., fluorescent tagging), this would greatly simplify and facilitate glycan analysis. The present invention provides such chromatographic media and methods of using them.

BRIEF SUMMARY OF THE INVENTION

In an exemplary embodiment, the present invention provides a true multimodal chromatographic medium (stationary phase) with unique properties of use in analysis of mixtures of glycans. The chromatographic medium of the invention includes an ion exchange chromatographic moiety and an uncharged chromatographic moiety bound to a solid substrate (e.g., particle, monolith). In various embodiments, the uncharged chromatographic moiety is one or more of a reverse phase chromatographic moiety and a hydrophilic interaction chromatographic moiety. The ion exchange moieties are weak or strong anion or cation exchange moieties. The chromatographic medium of the invention is a bimodal or trimodal chromatographic medium, which is suitable for analyzing a broad range of glycans, including those found in glycan-containing biomolecules.

Amongst its advantages, the multimodal chromatographic medium of the invention is a component of a superior approach for glycan analysis by HPLC and is based on a highly versatile chemistry platform providing desirable selectivity for different glycans. Moreover, compared to existing technologies, this invention provides superior resolution for complex glycans based on differences in charges, linkages, isomers and sizes. Because of the unique chemistry of the multimodal medium, the eluent from chromatographic separations of glycan on the medium is highly compatible with the detection of eluted glycans by fluorescence and mass spectroscopy.

In various embodiments, the invention provides methods of using this multimodal chromatographic medium in analyzing and/or separating glycan mixtures. In an exemplary embodiment, the invention provides a multimodal chromatographic method of separating a first glycan component from a second glycan component of glycan mixture. An exemplary method includes, (a) contacting the glycan mixture with a multimodal chromatographic medium comprising an ion exchange chromatographic moiety bound to a first substrate and an uncharged chromatographic moiety bound to a second substrate. The uncharged chromatographic moiety is selected from a reverse phase chromatographic moiety, a hydrophilic interaction chromatographic moiety and a combination thereof. As is typical in a chromatographic procedure, the glycan mixture is eluted from the column by contacting the medium and the medium-bound glycan with an eluent under conditions effective to achieve the separation of at least two components of the glycan mixture. In an exemplary embodiment, the said eluent comprises an electrolyte appropriate for use in anion exchange or cation exchange chromatography and which is compatible with the chromatographic medium.

In various embodiments, the present invention also provides methods for preparing the chromatographic media of the invention by reaction between activated analogues of the ion exchange and uncharged chromatographic moieties with complementary reactive groups on a solid support.

Also provided in selected embodiments of the invention are chromatographic devices, e.g., columns, containing the multimodal medium of the invention, and methods of using the medium and such devices to perform chromatographic separations and analysis of glycans.

In an exemplary embodiment, the invention provides a chromatographic system, which includes a separation device containing a chromatographic medium of the invention. The system optionally includes further components of use in performing a chromatographic separation of a glycan, e.g., a mass spectrometric or fluorescent detector.

Other objects, advantages and aspects of the invention are provided in the detailed description below.

BRIEF DESCRIPTION OF THE DRAWINGS

FIG. 4 is an LC-MS analysis of unlabeled N-glycans from bovine fetuin using a WAX/HILIC (Phase 22, 1.9 μm) column. Unlabeled glycans are separated based on charge, size and polarity. All the glycan peaks are detected by MS detection in negative mode with a mass scan range of 400-2200 Dalton. The N-glycan profiles of unlabeled glycans are different quantitatively than the labeled glycans from the same sample of bovine fetuin. For example, the quantitative profile of di-sialylated glycan peaks 7-12 for unlabeled glycans in FIG. 4 is different from the 2AB-labeled de-sialylated glycan peaks of 11-15 in FIG. 3A.

DETAILED DESCRIPTION OF THE INVENTION

I. Introduction

Figure 1:
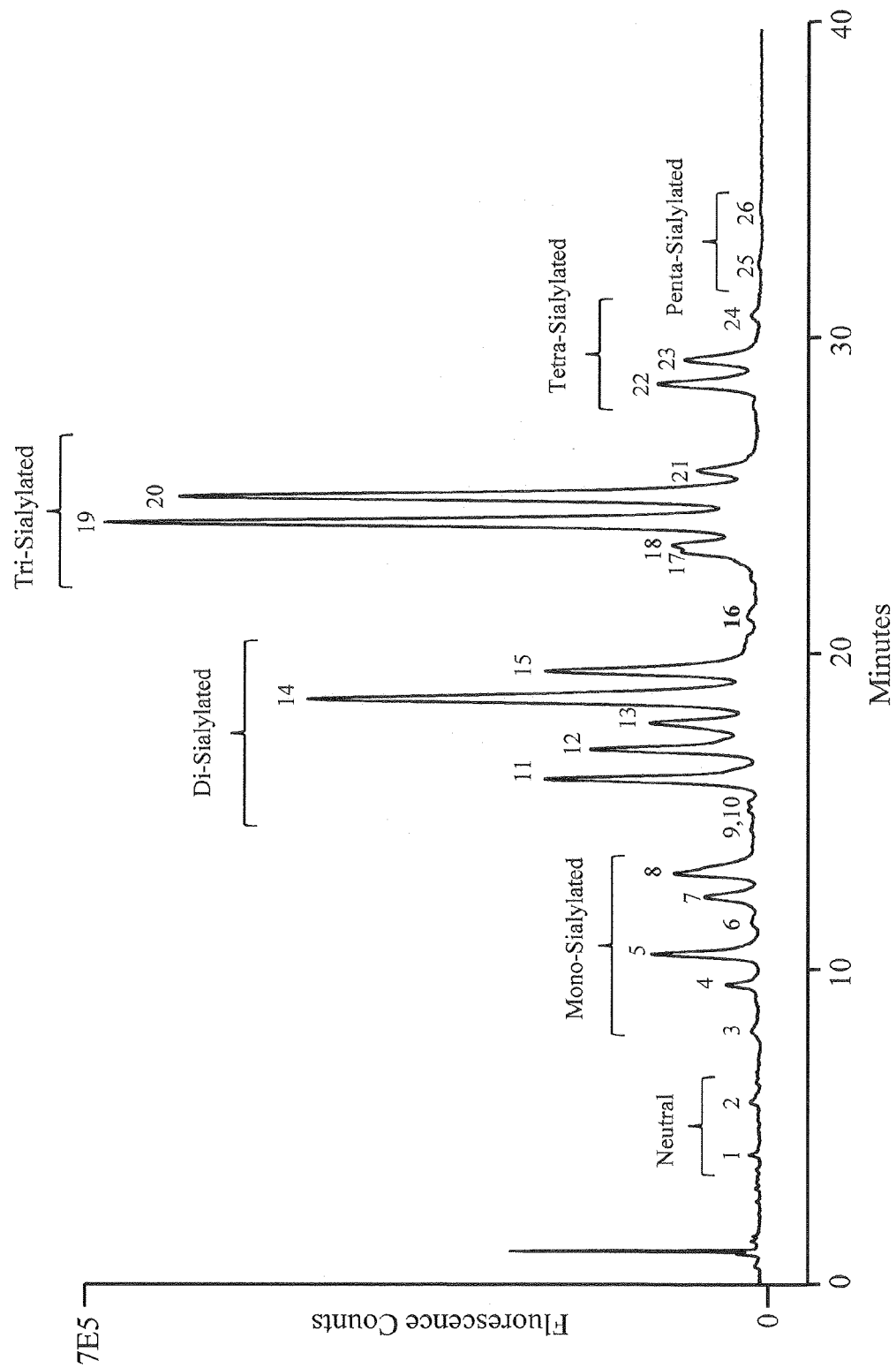
FIG. 1 is a chromatogram showing separation of 2AB-linked N-glycans from bovine fetuin by a column packed with WAX/HILIC (Phase 22, 1.9 μm). The peaks are detected by fluorescence detection. The chromatography was performed on the Ultimate-3000 UHPLC instrument. Neutral glycan peaks are eluted before monosialylated, monosialylated glycans are eluted before disialylated, di-sialylated species are eluted before tri-sialylated peaks, tri-sialylated before tetra-sialylated and tetra-siaylated are eluted before penta-sialylated species.

The art of liquid column chromatography is an old and well-known means for separating a material from a sample and for analyzing the components of a sample. Depending upon the sample and materials to be separated therefrom, one or more of a variety of modes of liquid column chromatography is used to effect the separation. Such chromatographic modes include size exclusion (SEC), ion-exchange, reversed phase, normal phase, hydrophilic interaction, hydrophobic interaction, affinity, donor-acceptor, ion-pair and chiral separation chromatography.

Combinations of different separation modalities can also be utilized in separation and analysis. Mixed-mode chromatography is a type of chromatography in which a chromatographic medium interacts with solutes (analytes) through more than one interaction mode. Mixed-mode chromatography media can combine either IEX and RP properties or IEX and HILIC properties. Mixed-mode chromatography can provide high resolution, adjustable selectivity, high sample loading, no need for ion-pairing agents (MS-compatibility), and the ability to replace two conventionally corresponding columns in certain circumstances.

Many bimodal separations fail when used with a large number of biological samples where biopolymers, like proteins or nucleic acids, are present along with small molecules, such as drugs, metabolites, pollutants, exo- and endotoxins, etc. Since sample pretreatment, like solvent extraction, solid phase extraction or ultrafiltration, is time-consuming and tedious, new chromatographic media have been developed which prevent contact between the groups used for separation in the reversed phase or ion-exchange chromatography. Media that have very small pores preventing large molecules from penetration into the bead (total exclusion), are mostly used. Clogging of the column by proteins stuck on the bead surface is inhibited by providing the surface with hydrophilic groups. This approach was reviewed recently (Pinkerton T. C., *J. Chromatogr.*, 544, (1991) 13; Haginaka J., *Trends Anal Chem.*, 10, (1991) 17). It may be called pseudomultimodal as one of the modes is actually not a chromatography but a simple filtration-like separation (total exclusion of all molecules exceeding a size limit).

The current invention provides chromatographic media with unique chromatographic properties, which are useful as chromatographic stationary phases for the chromatographic separation and analysis of glycans, and solid-phase extraction (SPE). In certain embodiments, the chromatographic medium of the invention includes two or more different chromatographic moieties having anion-exchange capabilities, cation-exchange capabilities, reverse phase capabilities or hydrophilic interaction capabilities. In various embodiments, the two or more different chromatographic moieties are bound to the same unit of the solid support (e.g., to the same particle). In other embodiments, the medium is formed by combining two or more materials having one or more chromatographic moiety bound to the same unit of the solid support.

In exemplary embodiments, the invention also provides methods of using the medium of the invention to separate and analyze mixtures of glycans, devices of use in these methods and systems incorporating such devices.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Abbreviations

Weak anion exchange ("WAX"); Strong Anion Exchange ("SAX"); Weak Cation Exchange ("WCX"); Strong Cation Exchange ("SCX"); Hydrophilic Interaction Liquid Chromatography ("HILIC"); 2-aminobenzamide (2AB); 2-aminobenzoic acid (2AA); Deionized (D.I.).

III. Definitions

Where substituent groups are specified by their conventional chemical formulae, written from left to right, they optionally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". The term "alkyl" can also mean "alkylene" or "alkyldiyl" as well as alkylidene in those cases where the alkyl group is a divalent radical.

The term "alkylene" or "alkyldiyl" by itself or as part of another substituent means a divalent radical derived from an alkyl group, as exemplified, but not limited, by —$CH_2CH_2CH_2$— (propylene or propane-1,3-diyl), and further includes those groups described below as "heteroalkylene." Typically, an alkyl (or alkylene) group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —OS(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The terms "substrate" and "support" or "solid support" are used interchangeably.

When compounds of the present invention contain relatively basic or acidic functionalities, salts of such compounds are included in the scope of the invention. Salts can be obtained by contacting the neutral form of such compounds with a sufficient amount of the desired acid or base, either neat or in a suitable inert solvent. Examples of salts for relative acidic compounds of the invention include sodium, potassium, calcium, ammonium, organic amino, or magnesium salts, or a similar salts. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science* 1977, 66: 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms "average diameter of the particle", "particle size", "average particle size", "median particle size", or any grammatical variation thereof refers to the particle size specification for a substrate (solid-support) of the invention. Particle-sizes are typically provided by the manufacturer. Particle sizes can refer to any type of particle including spherical and irregular-shaped particles.

"Mobile phase" and "eluent" are used interchangeably referring to a liquid that moves dissolved components (e.g., a glycan) of a mixture that is to be separated through a chromatographic column or other separation device. The mobile phase often contains more than one compound and is a mixture of different solvents or a solution of salts, acids, bases, etc.

"Solvent" is a liquid organic compound (e.g., a single compound). An exemplary solvent is at least partially water miscible. In various embodiments, a solvent is fully water miscible. In various embodiments, "solvent" refers to acetonitrile.

"Mobile phase strength" refers to the strength of the mobile phase in terms of, e.g., polarity, organic modifier concentration in reversed phase chromatography, buffer ionic strength in ion-exchange chromatography or hydrophilic interaction chromatography. In an exemplary embodiment, this term refers to the ionic strength of the mobile phase.

An exemplary mobile phase of use in the present invention includes from about 2 mM to about 30 mM of an electrolyte in combination with from about 50% to about 85% solvent (e.g., acetonitrile). In an exemplary embodiment, this eluent is used to separate glycans in a HILIC/WAX protocol. A further exemplary mobile phase of use in the present invention includes from about 2 mM to about 30 mM of an electrolyte in combination with from about 0% to about 50% solvent (e.g., acetonitrile). In an exemplary embodiment, this eluent is used to separate glycans in a RP/WAX protocol.

An "eluate" is the effluent of a separation device incorporating a chromatographic medium of the invention.

The term "electrolyte", as used herein, refers to an ionic component of a mobile phase, e.g., a buffer.

"Gradient" is a change in the composition of a mobile phase with time.

"Chromatographic medium" refers to a composition of matter having a binding site on a solid support.

"Binding site", "chromatographic moiety" and "chromatographic binding site" are used interchangeably to refer to a moiety on the chromatographic medium of the invention capable of binding to a glycan analyte.

"Glycan" refers to mono-meric, di-meric and higher "-meric" saccharides, oligosaccharides and polysaccharides. The term "glycan" also refers to species that include a glycan component, e.g., glycolipids, glycopolymers and glycopeptides. In an exemplary embodiment, the glycan mixture is a mixture of saccharides. An exemplary glycan includes one or more sialic acid attached moieties.

"Saccharide" is a species of glycan, which does not include a lipid or polypeptide moiety within its structure.

Terms referring to the magnitude of ion strength (e.g., of an eluant) are used in the present application. As used herein, the term "low ionic strength" refers to a concentration of an electrolyte component of a solution of less than or equal to about 30 mM. The term "high ionic strength" refers to a concentration of an electrolyte component of a solution of greater than or equal to about 100 mM. Correspondingly, "medium ionic strength" refers to a concentration of an electrolyte component of a solution that is greater than about 30 mM and less than about 100 mM.

Terms referring to the concentration of a solvent in an aqueous solution (e.g., of an eluant) are used in the present application. As used herein, the term "low solvent" refers to a concentration of a solvent in an aqueous solution of less than or equal to about 50%. The term "high solvent content" refers to a concentration of a solvent in an aqueous solution of greater than about 50%.

IV. Chromatographic Medium

In an exemplary embodiment, the invention provides a multimodal chromatographic medium. An exemplary medium has both charged and uncharged binding sites. In an exemplary embodiment, the medium includes two binding sites that operate by different modes, e.g., ion exchange, and RP or HILIC.

An exemplary multimodal chromatographic medium of the invention includes one or more strong anion exchange, weak anion exchange, strong cation exchange and/or weak cation exchange binding sites in combination with one or more reverse phase and/or hydrophilic interaction chromatography binding site. In an exemplary embodiment, the sites interact with one or more glycans in a mixture of glycans in a manner that allows separation of glycans in the mixture and analysis of the glycan mixture.

In various embodiments, the ion exchange moiety is an amine.

In an exemplary embodiment, the uncharged second binding site is a hydrophilic interaction site and is a urea, e.g., an uncharged urea moiety.

In an exemplary embodiment, the invention provides a chromatographic medium that has an anion exchange site (e.g., a WAX binding site) and a HILIC binding site and a particle size of about 3 µm. In another exemplary embodiment, the chromatographic medium of the invention has an anion exchange site, and a RP binding site and the particle size is about 1.9 µm.

In various embodiments the medium includes both first and second ion exchange binding sites. Exemplary first and second binding sites are different sites based on moieties that are structurally different from each other. In an exemplary embodiment, the first ion exchange binding site is an anion exchange binding site and said second ion exchange binding site is a cation exchange binding site.

The chromatographic medium also includes one or more uncharged binding site and, similar to the ion-exchange sites, when there are two or more uncharged binding sites, they are based on moieties having structures that are different from each other.

In an exemplary embodiment, the medium of the invention includes a cation binding site, an anion binding site and one or both of a reverse phase binding site and a hydrophilic interaction binding site.

The binding sites are bound to the substrate directly or through a linker. In an exemplary embodiment, the ion exchange chromatographic moiety is bound to the first substrate through a first linker moiety. In various embodiments, the uncharged chromatographic moiety is bound to the second substrate through a second linker moiety.

In various embodiments, the first linker moiety and the second linker moiety are separate chemical species so that the ion exchange chromatographic moiety and the uncharged chromatographic moiety can be independently linked to the first substrate and the second substrate, respectively. The first substrate may be the same as the second substrate, or alternatively the first and second substrates may be different. Independently linked means that the ion exchange chromatographic moiety and the uncharged chromatographic moiety are not attached to a common shared linker group. In addition, the independently linked ion exchange chromatographic moiety and uncharged chromatographic moiety are not linked directly to each other.

Linkers of use in the compositions of the invention can have any useful structure. For example, in an exemplary embodiment, either or both of the first linker moiety and/or the second linker moiety is a substituted or unsubstituted alkyl or heteroalkyl moiety. The linker is of any useful length. Exemplary linkers of use in the compounds of the invention include those of from about 3 carbons to about 40 carbons, e.g., 8 carbons to about 30 carbons in length. When the linker is substituted or unsubstituted heteroalkyl, the carbon chain is interrupted by one or more heteroatom, however, the overall length of the linker is from about 3 atoms to about 40 atoms in length.

In an exemplary embodiment, the ion exchange binding site and the first linker have the formula:

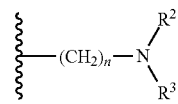

wherein $R^2$ and $R^3$ are independently selected from H, substituted or unsubstituted alkyl and substituted or unsubstituted heteroalkyl; and n is an integer from 3 to 30.

When the substrate is a silica substrate, in an exemplary embodiment, the binding site, linker and the moiety on the substrate to which the linker is bound have the formula:

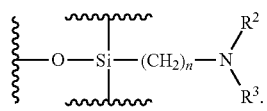

The first and second substrate can be the same substrate (e.g., same particle) or different substrates (e.g., different particles).

In a further exemplary embodiment, the binding site and the linker have the formula:

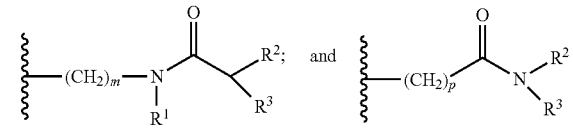

wherein $R^1$, $R^2$ and $R^3$ are independently selected from H, substituted or unsubstituted alkyl and substituted or unsubstituted heteroalkyl; and m and p are integers independently selected from 8 to 40.

In an exemplary embodiment in which the substrate is silica, the binding site, linker and the moiety on the substrate to which the linker is attached has the formula:

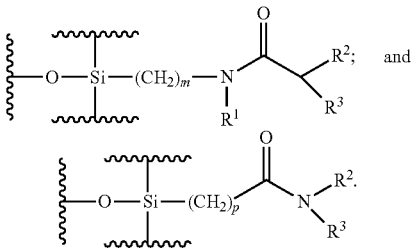

In each of the structures above, $R^1$, $R^2$ and $R^3$ are as described in the preceding paragraphs.

Figure 10:
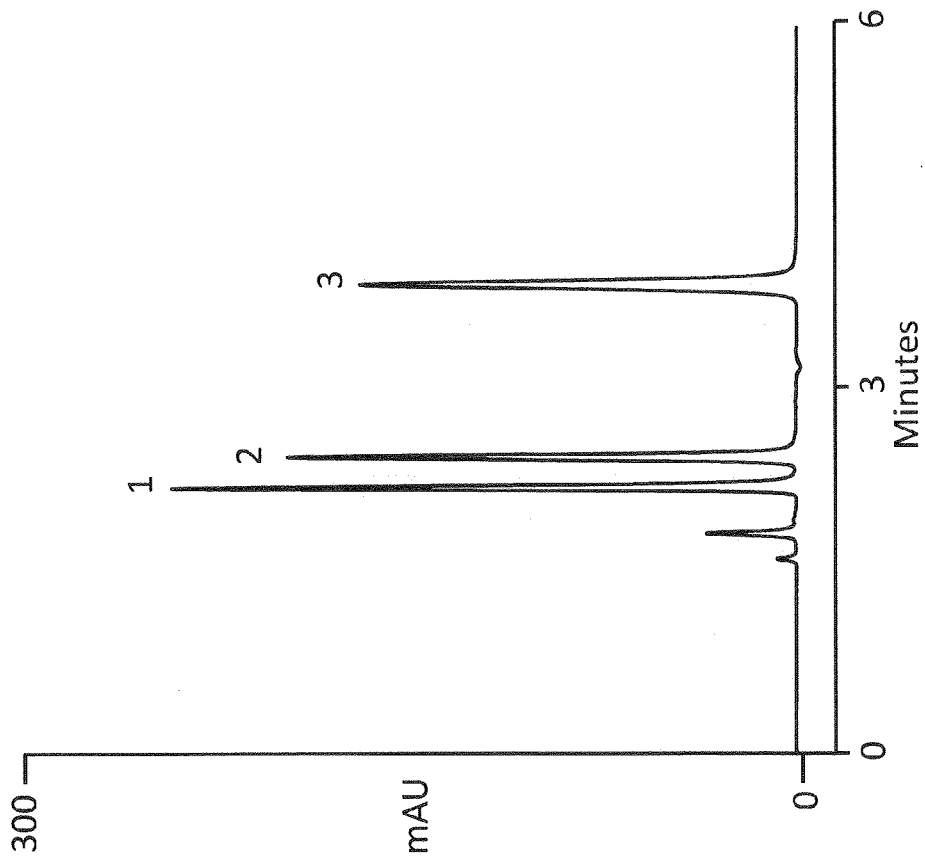
FIG. 10 is a chromatogram of the anion-exchange capacity determination of HILIC/anion-exchange mixed-mode phase. Column: Phase 22 (1.9-µm); Dimension: 2.1×150-mm; Mobile Phase: Acetonitrile/100 mM ammonium acetate buffer, pH5=90/10 (v/v); Flow rate: 0.21 mL/min; Injection volume: 1 µL; Temperature: 30° C.; Detection: UV at 220 nm; Peaks: 1. acetaminophen; 2. salicylic acid; and 3. acetyl salicylic acid.

In an exemplary embodiment, the invention provides a multimodal chromatographic medium, comprising: (a) a particulate silica substrate; (b) a first ion anion exchange binding site bound to said substrate; and (c) an uncharged binding site which is a member selected from a hydrophilic interaction chromatographic binding site, a reverse phase chromatographic binding site and a combination thereof also bound to said substrate, wherein said medium provides a chromatogram of a test sample according to FIG. 10 under the chromatographic conditions: (i) a column having the dimension 2.1×150 mm packed with said medium; (ii) a mobile phase of acetonitrile/100 mM ammonium acetate buffer, pH=5, 90:10 (v/v); (iii) a flow rate of about 0.21 mL/min; (iv) an injection volume of about 1 µl; (v) a temperature of said column of about 30° C.; and (vi) UV detection at about 220 nm, wherein the test sample consists essentially of acetominophen, salicylic acid, and acetyl salicylic acid in a diluent.

Figure 8:
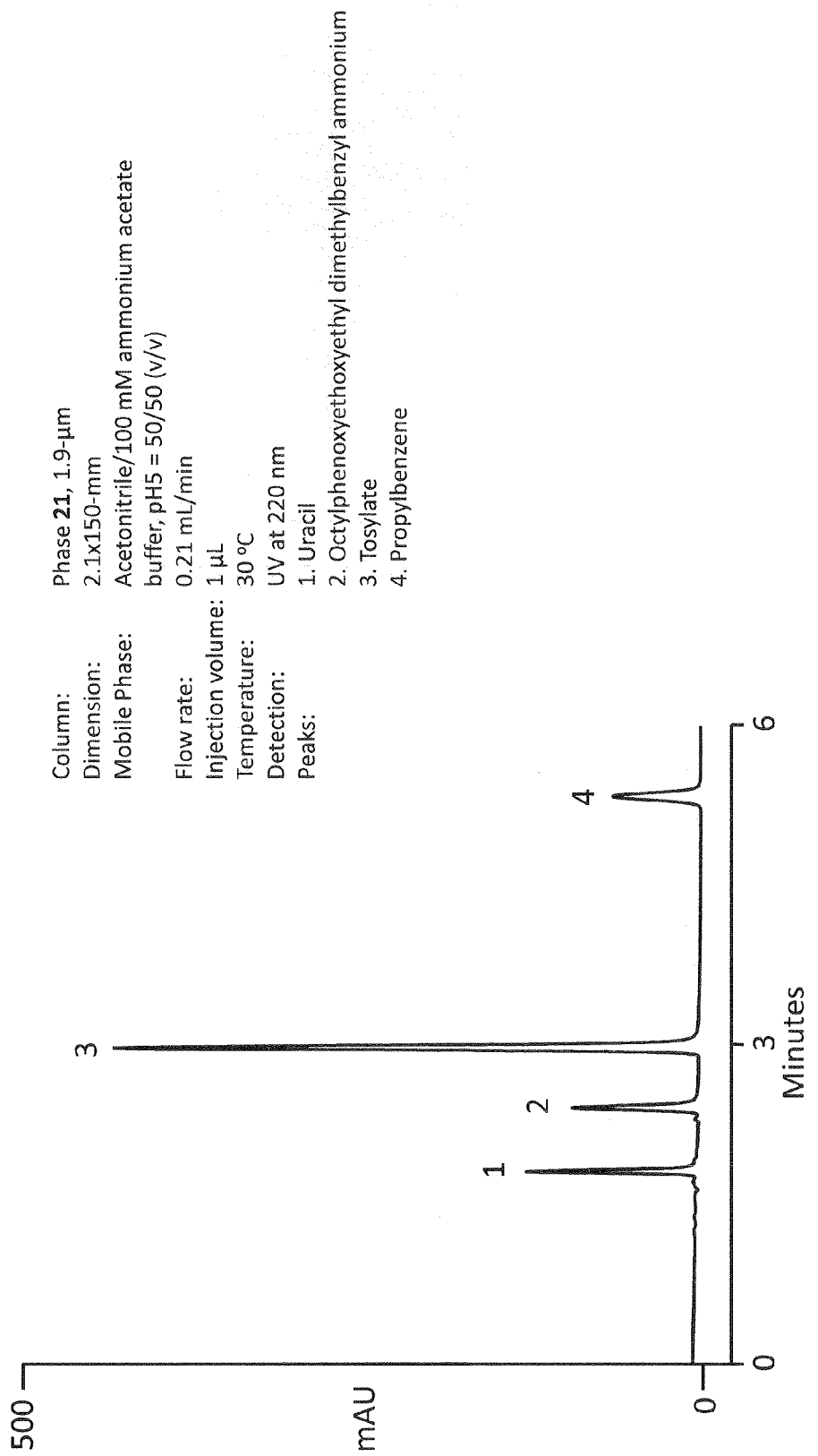
FIG. 8 is a chromatogram of the anion-exchange capacity determination for anion-exchange/reverse-phase mixed-mode phase. Column: Phase 21 (1.9-µm); Dimension: 2.1×150-mm; Mobile Phase: Acetonitrile/100 mM ammonium acetate buffer, pH5=50/50 (v/v); Flow rate: 0.21 mL/min; Injection volume: 1 µL; Temperature: 30° C.; Detection: UV at 220 nm; Peaks: 1. uracil; 2. octylphenoxyethoxyethyl dimethylbenzyl ammonium; 3. sodium tosylate; and 4. propylbenzene.

In various embodiments, the invention provides a multimodal chromatographic medium, comprising: (a) a particulate silica substrate; (b) a first anion exchange binding site bound to said substrate; and (c) an uncharged binding site which is a reverse phase chromatographic binding site also bound to said substrate, wherein said medium provides a chromatogram of a test sample according to FIG. 8 under the chromatographic conditions: (i) a column having dimension 2.1×150-mm packed with said medium; (ii) a mobile phase of acetonitrile/100 mM ammonium acetate buffer, pH=5=50/50 (v/v); (iii) a flow rate of about 0.21 mL/min; (iv) an injection volume of about 1 µL; (v) a column temperature of about 30° C.; and (vi) UV detection at about 220 nm, wherein the test sample consists essentially of uracil, octylphenoxyethoxyethyl dimethylbenzyl ammonium, sodium tosylate, and propylbenzene.

In an exemplary embodiment, the invention provides a multimodal chromatographic medium, comprising: (a) a particulate silica substrate; (b) a first ion exchange binding site bound to said substrate; (c) an uncharged binding site which is a member selected from a hydrophilic interaction chromatographic binding site, and a reverse phase chromatographic binding site also bound to said substrate; and (d) a member selected from a second ion exchange binding site and a second uncharged binding site which is a member selected from a hydrophilic interaction chromatographic binding site, and a reverse phase chromatographic binding site also bound to the substrate.

A capacity factor, k', can be used to characterize a chromatographic material in a column, as shown in Equation 1.

$$k' = \frac{t_i - t_m}{t_m} \quad \text{(Eq. 1)}$$

The terms $t_m$ represent the time required for the mobile phase to pass through the column and $t_i$ represents the retention time for a particular peak corresponding to the compound i on the chromatogram. A selectivity factor a can be calculated to describe the separation of two chemical species, as shown in Equation 2.

$$\alpha = \frac{k_{A'}}{k_{B'}} \quad \text{(Eq. 2)}$$

The terms $k_A'$ represent the capacity factor for the chemical species A and $k_B'$ represent the capacity factor for the chemical species B. In an exemplary embodiment, α may range from about 0.15 to about 0.60 where chemical species A is tosylate and chemical species B is propylbenzene.

In an exemplary embodiment, a may range from about 0.10 to about 0.40 where chemical species A is acetaminophen and chemical species B is acetyl salicylic acid according to Equations 1 and 2.

Solid Support

The substrate or solid support of the chromatographic medium of the invention can be any material (e.g., particles) useful as a chromatographic medium/packing material for chromatography including porous and non-porous solids.

In various embodiments, the solid support is selected from particulates or monoliths. Exemplary particles include silica particles, silica/organo hybrid particles, core-shell particles, $TiO_2$ particles, $ZrO_2$ particles, and $Al_2O_3$ particles.

Exemplary substrates include cross-linked and non-crosslinked polymers. Other substrates include silica-based (e.g., silicon oxide), titanium-based (e.g., titanium oxide), germanium-based (e.g., germanium oxide), zirconium-based (e.g., zirconium oxide) and aluminum-based (e.g., aluminum oxide), carbonized materials and metals.

The solid support may be formed from any synthetic resin material. Exemplary synthetic polymer ion-exchange resins include poly(phenol-formaldehyde), poly(acrylic acid), poly(methacrylic acid), polynitriles, amine-epichlorohydrin copolymers, graft polymers of styrene on polyethylene or polypropylene, poly(2-chloromethyl-1,3-butadiene), poly(vinylaromatic) resins such as those derived from styrene, α-methylstyrene, chlorostyrene, chloromethylstyrene, vinyltoluene, vinylnaphthalene or vinylpyridine, corresponding esters of acrylic acid and methacrylic acid, and similar unsaturated monomers, mono-vinylidene monomers including the monovinylidine ring-containing nitrogen heterocyclic compounds, and any copolymers of the above resins. Additional examples include glycidyl acrylate-based and glycidyl methacrylate-based materials (e.g., 2-glycidyloxyethyl methacrylate, vinylbenzyl glycidyl ether, 2-(4-vinylbenzyloxy)ethyl glycidyl ether) as well as those derived from vinylbenzyl chlorides, vinylbenzyl alcohols, 2-(4-vinylbenzyloxy)ethanol, polyacrylamides, polyvinylalcohols, polyvinylformamides.

Any of the above materials can optionally be co-polymerized with monomers incorporating ionic or ionizable, reverse-phase and HILIC functionalities.

In one embodiment, the support comprises cross-linked polymers or copolymers. An exemplary copolymer is styrene-divinylbenzene copolymer (e.g., PS-DVB). In one example, the styrene-divinylbenzene copolymer contains between about 2% to about 100% divinylbenzene monomer by weight. In another example, the styrene-divinylbenzene copolymer contains between about 25% to about 80% divinylbenzene monomer by weight. The copolymer can be prepared, for example, according to the method of Ikada et al., *Journal of Polymer Science*, Vol. 12, 1829-1839 (1974) or as described in U.S. Pat. No. 4,382,124 to Meitzner, et al.

In one example, the solid support includes a silica, alumina, zirconia, or titania-polymeric resin hybrid material. Exemplary silica-organic hybrids are described in U.S. Pat. No. 6,528,167 and U.S. Patent Application Publication 2006/0070937 (application Ser. No. 11/240,695), the disclosures of which are incorporated herein by reference for all purposes.

In one embodiment, a solid support of use in the present invention is formed by well known suspension polymerization techniques. In this example, the particles are typically derived from a monomer mixture, which is insoluble in the solvents with which they will be contacted. Exemplary substrates are formed by heating and stirring a suspension of monomers in a suitable solvent in the presence of a suitable emulsifying agent. Alternatively, the polymerization may be carried out by a suspension, bulk or solution process followed by grinding the resin to a desired size by mechanical means (e.g., ball mills, rod mills or the like).

The solid support can be of any form, including particulates (e.g., cubic, granular, spherical, essentially spherical; e.g., resin beads), chips, chunks, blocks, monoliths and the like. When the substrate is in particulate form, the particles (e.g., irregular-shaped or bead-shaped, e.g., essentially spherical) have a median particle size (i.e., diameter). In one example, the median particle size of the substrate (e.g., spherical silica gel) is between about 0.1 (e.g., silica microspheres) and about 10,000 µm (microns). In one example, the median particle size of the substrate is between about 1 and about 5000 microns, between about 1 and about 1000 microns, between about 1 and about 500 microns, between about 1 and about 400 microns, between about 1 and about 300 microns, between about 1 and about 200 microns or between about 1 and about 100 microns. In yet another example, the median particle size of the substrate is between about 1 and about 80 microns, between about 1 and about 70 microns, between about 1 and about 60 microns, between about 1 and about 50 microns, between about 1 and about 40 microns, between about 1 and about 30 microns, between about 1 and about 20 microns or between about 1 and about 10 microns. In other example, the median particle size of the substrate particles is between about 10 and about 100 microns, between about 10 and about 80 microns, between about 40 and about 200 microns, between about 40 and about 100 microns, between about 40 and about 80 microns, between about 60 and about 200 microns, between about 60 and about 100 microns, between about 70 and about 200 microns, between about 80 and about 200 microns, between about 100 and about 200 microns, between about 200 and about 600 microns, between about 200 and about 500 microns or between about 200 and about 400 microns.

In an exemplary embodiment, the solid support is a particle of about 1.5 µm to about 20 µm, e.g., from about 1.9 µm to about 3 µm. In various embodiments, the solid support is about 1.9 µm. In various embodiments, the solid support is about 3 µM.

Generally, substrate particles useful in any packed bed chromatographic application (e.g., LC, HPLC or ultra-pressure chromatography) are suitable for use in the chromatographic media of the invention.

In various examples, the support is in particulate form, and multiple support particles are disposed in a packed bed. For example, a plastic or metal column is packed with the support particles. In an exemplary embodiment, the medium of the invention is composed of two or more chromatographic media. For example, one chromatographic medium consists of particles with an ion exchange binding site. This chromatographic medium is mixed with a second chromatographic medium having RP or HILIC binding sites. As will be appreciated multiple chromatographic media, each with a different binding site, are combinable to form a chromatographic medium of the invention.

In various examples, the solid support particles are essentially "homodisperse" or essentially "homodisperse", which indicates that the particle size of the majority of the particles (e.g., 80, 90 or 95% of the particles) does not vary substantially (e.g., not more than 50%) below or above the median particle size (M). In an exemplary monodisperse substrate particle population, 90% of the particles have an average particle size of between about 0.5 times M and about 1.5 times M. In an exemplary embodiment, such a particle has a size from about 1.9 µm to about 3 µm. In various embodiments, such a particle is about 1.9 or about 3 µm.

In another example, the substrate is an inorganic or organic monolith. In one example the solid support includes a silica monolith. In another example, the solid support includes an alumina monolith. In yet another example, the solid support includes a zirconia monolith. In a further example, the solid support includes a titania monolith. Exemplary monolithic materials based on organic compositions and methods of preparing such materials are described in U.S. Pat. Nos. 5,130,343; 5,929,214; 5,728,457; 5,260,094; 6,887,384; 5,334,310; 7,303,671; 5,453,185 and 7,074,331.

An exemplary solid support of use in the present invention is assembled by functionalizing a particle with the desired binding site by reaction between moieties of complementary reactivity on the moiety bearing the binding site and the solid support.

In another exemplary embodiment the invention provides an aggregated chromatographic material incorporating the chromatographic medium set forth herein. For example, a chromatographic medium of the invention is contacted with a second ion exchange medium having an opposite charge under conditions promoting the electrostatic aggregation of the two ion exchange materials, thereby forming an electrostatically aggregated ion exchange medium. In various embodiments, the chromatographic medium of the invention is negatively charged and the second ion exchange medium is positively charged. In another exemplary embodiment, the ion exchange chromatographic medium of the invention is positively charged and the second ion exchange chromatographic medium is negatively charged. Such aggregated media are described in, for example, Small, et al. U.S. Pat. No. 4,101,460 in which is described finely divided insoluble materials bound by electrostatic attraction to substrate particles having ion exchange sites. Either or both the chromatographic medium of the invention and the second ion exchange chromatographic medium can include within their structure a RP and/or HILIC binding site.

V. Devices and Systems

The invention also provides devices and systems incorporating the chromatographic media of the invention. Thus, in an exemplary embodiment, the chromatographic medium is in a flow-through bed suitable for use as a chromatographic device. In an exemplary embodiment, the invention provides a chromatography column packed with the chromatographic medium of the invention.

In an exemplary embodiment, the device is a column packed with a chromatographic medium of the invention. The column hardware in one embodiment of the invention includes rigid tubes to be used as chromatographic columns, with various shapes including cylindrical, conical, rectangular, and polygonal or an assembly of these tubes. The tube may be made from any conventional materials know in the art including metal, glass, silica, plastic or other polymers, more preferably the stainless steel or glass. The inner dimension of this tube can be from micrometers to meters in diameter, thickness, width, or depth. The chromatographic medium may span the entire cross-section area of the tube where the separation of the samples take place by passing through the tube axially or radially (Lee, W-C, et al, "Radial Flow Affinity Chromatography for Trypsin Purification", Protein Purification (book), ACS Symposium Series 427, Chapter 8, American Chemical Society, Washington, D.C., 1990.) depending on the mode of separation, more specifically the axial or direct flow chromatography or the radial flow chromatography. The inner surface of the column may be non-reactive or may be treated to increase adhesion to the surface of chromatographic medium. The tube can incorporate any usable fittings know in the art to connect it with other instruments, more specifically chromatography instruments.

In various embodiments, the invention provides a chromatographic system. In an exemplary embodiment, the system is a high performance liquid chromatography (HPLC) system. Exemplary systems include one or more separation device, which contains a chromatographic medium of the invention. An exemplary system includes one or more separation device in line and in fluidic communication with one or more device for regulating eluent supply to the separation device, e.g., an eluent generator, a pump; one or more detection device, e.g., a mass spectrometric and/or fluorescence detector; and one or more means of introducing a sample on to the separation device, e.g., a sample injection valve.

By way of illustration, exemplary systems for HPLC analysis typically include a chromatographic separation zone using an eluent containing an electrolyte, and an eluent suppression stage, followed by detection, typically performed by mass spectrometer or a fluorescence detector. In the chromatographic separation stage, glycan components of an injected sample are eluted from a separation column.

Eluent is supplied from a source, which can includes a vessel containing premade eluent or it can be generated by an eluent generator. Eluent generators are known in the art. An exemplary eluent generator is disclosed in U.S. Pat. No. 7,767,462.

VI. Methods

Method of Manufacture

The chromatographic medium of the invention can be made by any convenient method including, but not limited to, functionalizing a preformed substrate with a reactive moiety that includes the desired binding site(s), or polymerization of monomers functionalized with the desired binding site(s). The examples appended hereto provide exemplary methods for manufacturing a chromatographic medium of the invention.

In an exemplary embodiment, the chromatographic medium is a RP/WAX medium and the medium is prepared by reaction of moieties containing reverse phase and ion exchange binding sites with a substrate. A process for preparing an exemplary medium uses and excess of RP-containing moieties relative to those containing the ion exchange binding site. An exemplary ratio is from about 10-20:1 RP:ion exchange sites, e.g. from about 12-18:1. See, Examples 6 and 7. In various embodiments, the ion exchange binding site is an anion exchange site, e.g., a WAX site. An exemplary process for preparing a HILIC/WAX medium uses similar condition.

Methods of Chromatographic Analysis

The present invention also provides methods of performing chromatographic separations using the multimodal chromatographic media of the invention.

In an exemplary embodiment, the invention provides a multimodal chromatographic method of separating a first glycan component from a second glycan component of glycan mixture using a chromatographic medium of the invention. The method includes (a) contacting the glycan mixture with a multimodal chromatographic medium of the invention and an eluent. In an exemplary embodiment, the chromatographic medium has an ion exchange chromatographic moiety bound to a first substrate and an uncharged chromatographic moiety bound to a second substrate (e.g., a second substrate different from the first substrate, or the same substrate as that to which the first chromatographic moiety is bound). The uncharged chromatographic moiety is selected from a reverse phase chromatographic moiety, a hydrophilic interaction chromatographic moiety and a combination thereof. The glycan component of a glycan mixture is contacted with the chromatographic medium and the eluent under conditions effective to achieve a separation of two or more glycans in the glycan mixture. An exemplary eluent includes from about 1 mM to about 50 mM electrolyte. In various embodiments, the organic solvent is present in said eluent in an amount up to about 45%, 55%, 65%, 75%, 85% or 95% (v/v) of said eluent.

The method of the present invention can be practiced with any appropriate mobile phase. The mobile phases, which are used in liquid chromatography, are well known in the art. Suitable mobile phases generally are water, buffered aqueous salt solutions with or without un-buffered salt solutions, organic solvents and mixtures containing or more of these components. Specific examples include water/acetonitrile, water/methanol, water/propanol, and water/THF with an electrolyte (e.g., ammonium acetate, ammonium formate), TRIS—HCl buffer, TRIS—HCl buffer solution/NaCl, phosphate buffer/ammonium sulfate, acetonitrile/diethylamine, and hexane/methanol In an exemplary embodiment, the chromatographic separation is optimized by adjusting and controlling organic solvent, buffer concentration and/or the pH of the mobile phase, in the range of 0 to 95%, 1 to 100 mM and 1 to 10, respectively.

An exemplary eluent of use in the present invention is a composition that is compatible with analysis by mass spectrometry of the components of the glycan mixture without the need to desalt or otherwise manipulate the eluate containing glycans separated by a method of the invention.

In an exemplary embodiment, the composition of the eluent changes as the separation proceeds, i.e., the mobile phase is run as a gradient. When a gradient is utilized, the ratio of the components changes during the chromatographic process in a predetermined manner. During the elution stage, the solvent may also be changed to separate slightly different molecules from each other without changing the mode of separation. For example, during a reversed-phase mode the concentration of the solvent in the eluent may be increased in a step-wise fashion to detach, during each step, a different molecule from a surface group of the separation medium to which it has attached itself. The difference in the concentration of solvent between each step will depend on the solvent being used, the molecules to be separated, the active groups in the separation medium and the duration of the eluting stage.

In an exemplary embodiment, the gradient runs from about 85% solvent to about 30% solvent. Exemplary solvents include acetonitrile, methanol, THF and propanol. In various embodiments, the gradient runs from about 1 mM electrolyte to about 30 mM electrolyte. In an exemplary embodiment, the gradient runs from about 85% solvent and 1 mM electrolyte to about 55% solvent and about 30 mM electrolyte. An exemplary application for gradients according to this description includes WAX/HILIC separations of glycans.

In an exemplary embodiment, the gradient runs from about 0% solvent to about 50% solvent. Exemplary solvents include acetonitrile, methanol, THF and propanol. In various embodiments, the gradient runs from about 1 mM electrolyte to about 50 mM electrolyte. In an exemplary embodiment, the gradient runs from about 0% solvent and 1 mM electrolyte to about 50% solvent and about 50 mM electrolyte. An exemplary application for gradients according to this description includes WAX/RP separations of glycans.

Glycans that can be separated using the chromatographic medium of the invention and the methods of the invention include labeled and unlabeled glycans. The glycans can be charged or uncharged. Exemplary glycans include N- and O-glycans from various proteins and mucins. In various embodiments, the glycans are labeled or unlabeled reduced N-glycans from proteins, labeled or unlabeled non-reduced N-glycans from proteins, labeled or unlabeled reduced O-glycans from proteins, and labeled or unlabeled reduced O-glycans from mucins.

In various embodiments, the method separates two or more charged glycans, e.g., sulfated non-sulfated glycans, de-polymerized glycans from GAG, heparin fragments with 4 to 8 saccharides with/without defined sulfation, and phosphorylated glycans.

Samples separated using the chromatographic medium and methods of the invention can be from any source. Exemplary glycans are sourced from glycoproteins, monoclonal antibodies, recombinant glycoproteins and growth hormones, cellular, serum and plasma proteins, oncoproteins, glycopolymers, and plant proteins. The glycans can also be components of glycolipids (e.g., gangliosides, globosides and glycosphingolipids).

The chromatographic medium and methods of the invention are of use to quantitate the absolute or relative amounts of glycan components in a glycan mixture separated by a method of the invention. For example, the methods of the invention can be used to estimate the charge state of one or more glycans in the mixture (FIG. 6), estimate the total of one or more sialic acid-containing glycan and estimate the amount of α(2,3) and α(2,6) linked glycans.

In an exemplary embodiment, the media and methods of the invention are used to separate glycans of the ABO blood group (e.g., N-acetylgalactosamine, galactose) antigens (ABO(H)) and their variations, e.g., A1, A2, H-type 1, H-type 2, H-type 3, H-type 4, etc.). In another embodiment, the glycans separated are the Lewis blood group (human fucose-containing) antigens (e.g., sLex, Lex, Lea, sLea, repeating Lex, etc., on glycolipid, N- and O-glycan backbones, etc.).

The present invention also provides a method in which the separation process results in a chromatogram in which the first glycan component and the second glycan component have retention times proportional to their charge, such that a third glycan having a charge identical to that of the first glycan component or the second glycan component will have a retention time grouped with the glycan component of identical charge.

Figure 5:
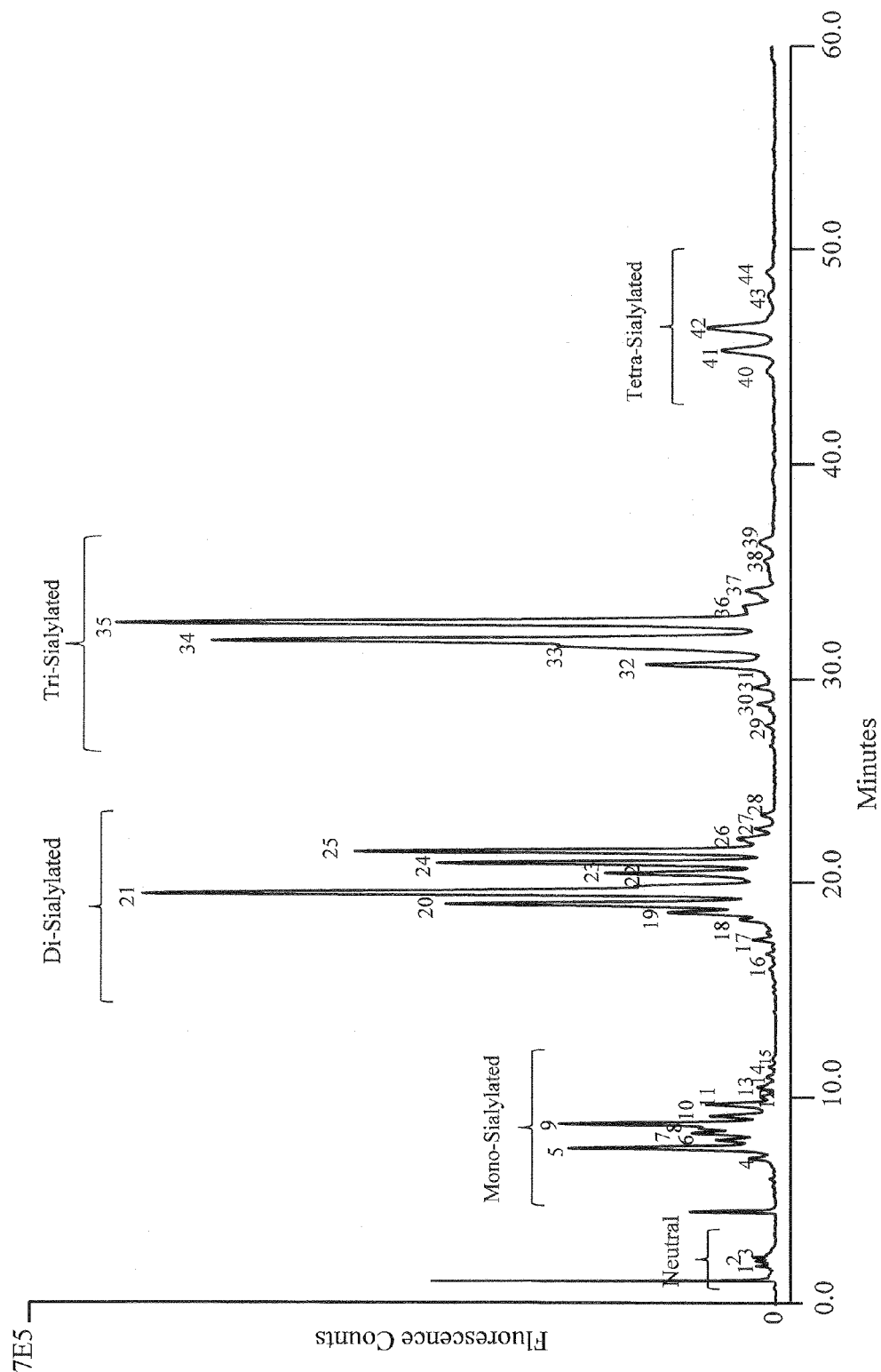
FIG. 5 is a separation of 2AB-N-glycans from bovine fetuin using WAX/RP (Phase 21, 1.9 μm) mixed mode columns. Glycans are separated with high resolution (as many as 40 peaks are resolved) based on charge, size isomers and polarity. This column provides a greater number of peaks (~44) for 2AB-labeled N-glycans from bovine fetuin than an exemplary commercial column (≤26 peaks) and WAX/HILIC (Phase 22, 1.9 μm) column as shown in FIG. 3B and FIG. 3A, respectively.

In an exemplary embodiment, two or more of the glycans of the glycan mixture are sialylated and the method results in a chromatogram in which sialylated glycans having the same number of sialic acid moieties are grouped together in the chromatogram. For example, FIG. 1 shows a chromatogram in which disialyted glycan are grouped together (e.g., peaks 9-16), as are trisialyted glycans (e.g., peaks 17-21). FIG. 5 also shows a chromatogram produced by a method of the invention in which disialyl glycans are grouped together (e.g., peaks 16-28), and triasialylated glycans are grouped together (e.g., peaks 29-39). Thus, the present invention provides a method for grouping charged glycans together during separation and on a chromatogram based upon their charge polarity and density.

In an exemplary embodiment, prior to analysis using a method of the invention, the glycan is separated from a polypeptide to which it is bound. Thus, the method includes step (b) in which prior to step (a), a first precursor glycan mixture is prepared by treating a solution of at least one glycoprotein with a glycosidase, thereby forming the first precursor glycan mixture. Exemplary glycosidase are selected from PNGase F, PNGase A and a combination thereof.

In various embodiments, the method includes one or more pre-analysis preparation steps to "clean up" a first precursor glycan mixture prior to its analysis, thereby forming a second precursor glycan mixture. The second precursor glycan mixture is analyzed using a chromatographic medium of the invention. An exemplary method includes the steps, (i) precipitating proteins in a first precursor glycan mixture, forming a mixture comprising precipitated proteins and a supernatant; (ii) pelleting the precipitated proteins by centrifuging the mixture of step (i), forming a two-phase mixture; (iii) removing the supernatant from the two-phase mixture, forming an isolated supernatant; and (iv) dialysing the isolated supernatant, thereby forming the second precursor glycan mixture. Alternatively, the first precursor glycan mixture is submitted to reverse phase high performance liquid chromatography, thereby forming said second precursor glycan mixture.

In an exemplary embodiment, the method of the invention further comprises (d), following step (c), preparing a labeled glycan mixture comprising a labeled analogue of the first glycan component and a labeled analogue of the second glycan component. Labeling with a detectable label is typically accomplished by submitting the second precursor glycan mixture to a mixture comprising a reactive, detectable label under conditions effective to label a glycan in the second precursor glycan mixture with the detectable label, thereby preparing the labeled glycan mixture. In an exemplary method, the glycan is labeled by reductive amination of a reducing group on the glycan with an analogue of the detectable label having a reactive amine moiety. As will be appreciated by those of skill in the art, the glycans of the first precursor glycan mixture can alternatively be labeled using recognized procedures.

In various embodiments, the method of the invention further comprises (d) following step (c), treating the second precursor glycan mixture with sialidase A, sialidase B or a combination thereof, thereby preparing the glycan mixture.

As they elute off of the medium of the invention, components of the glycan mixture are detected in a method of the invention further comprising, (e) following step (d), submitting the first glycan component and the second glycan component to analysis by mass spectrometry or fluorescence detection.

In exemplary embodiments, in which the glycan mixture includes labeled glycans these species are detected in a method further comprising, following step (a), submitting the labeled first glycan component and the labeled second glycan component to analysis by mass spectrometry or fluorescence detection.

Any detectable label can be used in the method of the invention. An exemplary detectable label is a fluorescent label. An exemplary fluorescent label is an aromatic amine, e.g., 2-aminobenzoic acid, 2-aminobenzamide, 2-aminopyridine, 8-aminonapthaline-1,3,6-trisulfonic acid, 2-aminoacridone, and 9-aminopyrene-1,3,6-trisulfonic acid.

Figure 2A:
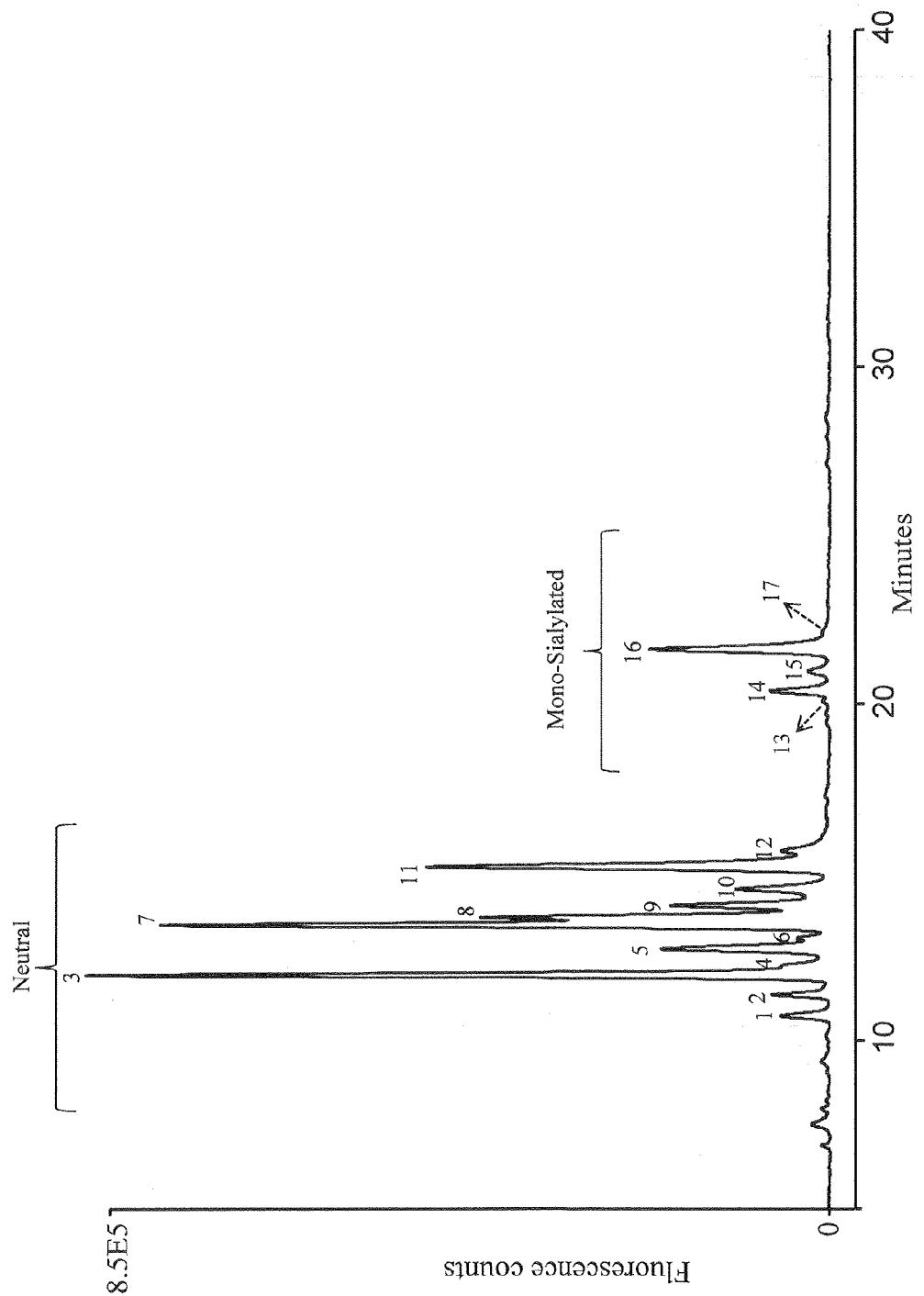
FIGS. 2A & 2B are chromatograms showing the separation of 2AA-linked N-glycans from human IgG by a column packed with WAX/HILIC (Phase 22, 1.9 μm) column. The separation was performed using binary gradient conditions using Ultimate 3000 UHPLC system. MS spectra were recorded with a Q-Exactive instrument. A. Peaks are detected by a fluorescence detector, B. Peaks are detected by MS detection in negative mode with the mass scan range from 400-2200 Dalton. The glycans in each peak are characterized by LC-MS/MS data from Simglycan software. The list of glycans present in IgG is shown in Table 1.
Figure 2B:
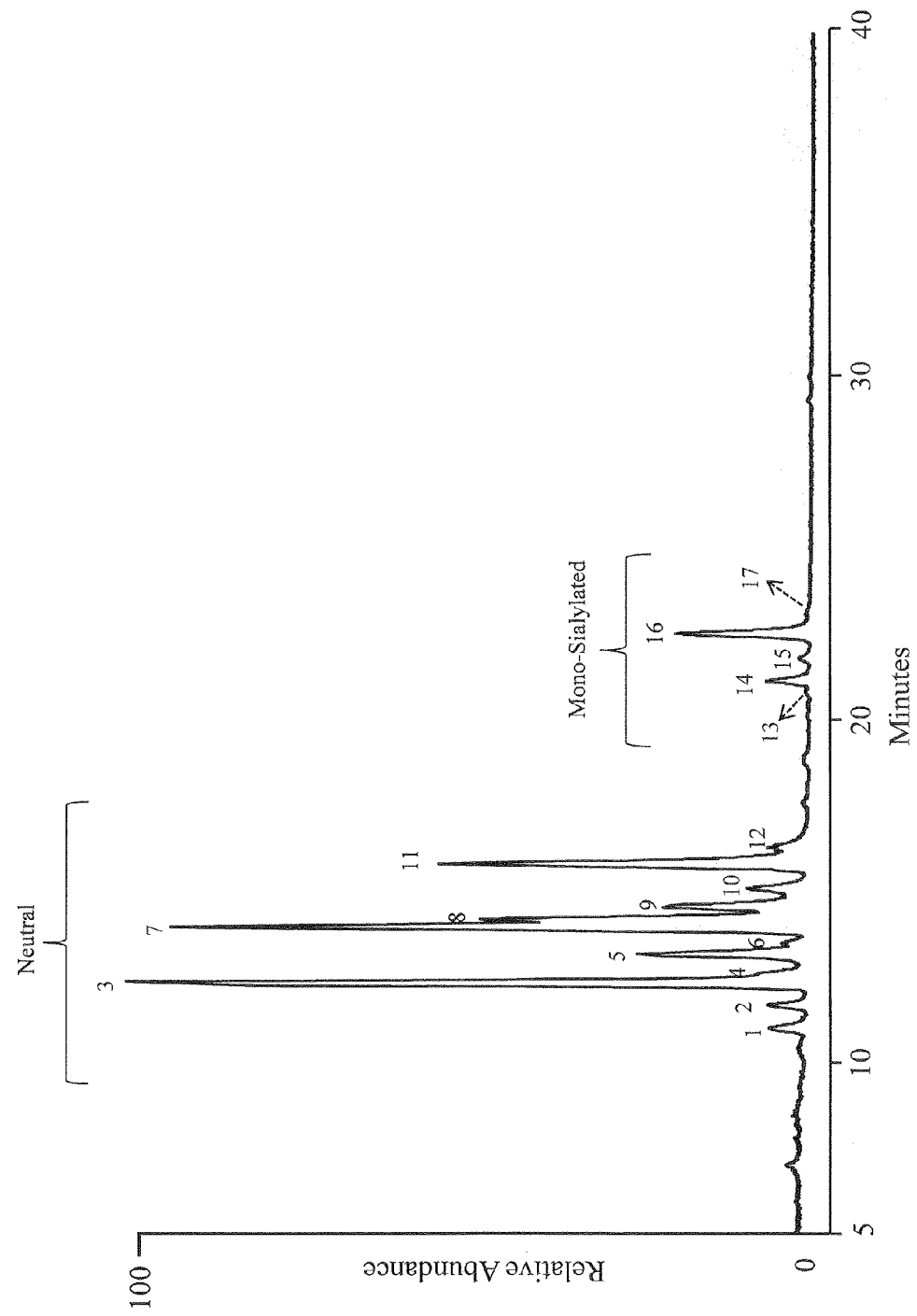

Also provided is a method of improving the chromatographic separation of an unsialylated first glycan and an unsialylated second glycan on a multimodal chromatographic medium. An exemplary medium is a medium of the invention comprising an ion exchange chromatographic moiety bound to a first substrate and an uncharged chromatographic moiety bound to a second substrate, which are the same or different substrates. As discussed herein, the uncharged chromatographic moiety is a reverse phase chromatographic moiety, a hydrophobic interaction chromatographic moiety or a combination thereof. The method includes, (a) derivatizing the first unsialylated glycan and the second unsialylated glycan with a detectable label comprising a charged moiety, forming a labeled first glycan and a labeled second glycan; and (b) contacting the multimodal chromatographic medium with the labeled first glycan and the labeled second glycan under conditions effective to separate the first and second labeled glycans. In an exemplary embodiment, the results of a separation according to this method are improved relative to a separation of the first unsialylated glycan and the second unsialylated glycan on the multimodal chromatographic medium. Thus, in various embodiments, the presence of the conjugated label improves the resolution of the method. FIG. 2.

In an exemplary embodiment, the first and second glycans are derivatized with a charged moiety that is not, per se, a detectable moiety (e.g., it is substantially non-fluorescent)

Devices

The mixed mode mixed-mode medium of the present invention is readily incorporated into separation devices, e.g., columns, and monoliths. In various embodiments, the device is a column packed with a particulate medium of the invention. Exemplary column internal diameter dimensions are from about 0.050 to about 2000 mm. Exemplary column lengths are from about 5 to about 10,000 mm. Exemplary columns of the invention include a mixed mode medium of the invention packed into a column with dimensions 2.1×150 mm, 2.1×50 mm, 3×150 mm, 1×150 mm, 0.4×150 mm, 2.1×

250 mm or 3×250 mm. Also provided are monoliths that incorporate the chromatographic medium of the invention.

Detection

The present methods provides chromatographic media and methods for separating glycans under conditions, which, in an exemplary embodiment, are compatible with detection of the glycans by mass spectrometry, fluorescence detection, UV detection, and/or aerosol based detection (e.g. charged aerosol detection, evaporative light scattering detection, etc.)

In an exemplary embodiment, one or more glycan in a glycan mixture separated by a method of the invention is labeled with a detectable label. Exemplary labels include those detectable by UV/Vis detection, fluorescence detection, and mass spectrometric detection. In various embodiments, the detection modality is UV/Vis and the detectable label is a UV-detectable chromophore. In various embodiments, the detection modality is fluorescence detection and the detectable label is a fluorophore. In an exemplary embodiment, the detection modality is mass spectrometry and the detectable label is a mass label.

In various embodiments, the selectivity of the chromatographic medium and the methods of the invention can be tuned based on the label conjugated to the one or more glycan of the glycan mixture (FIG. 2).

The following examples illustrate various embodiments of the invention in a non-limiting manner.

EXAMPLES

Example 1

Preparation of Compound 10

Figure 7:
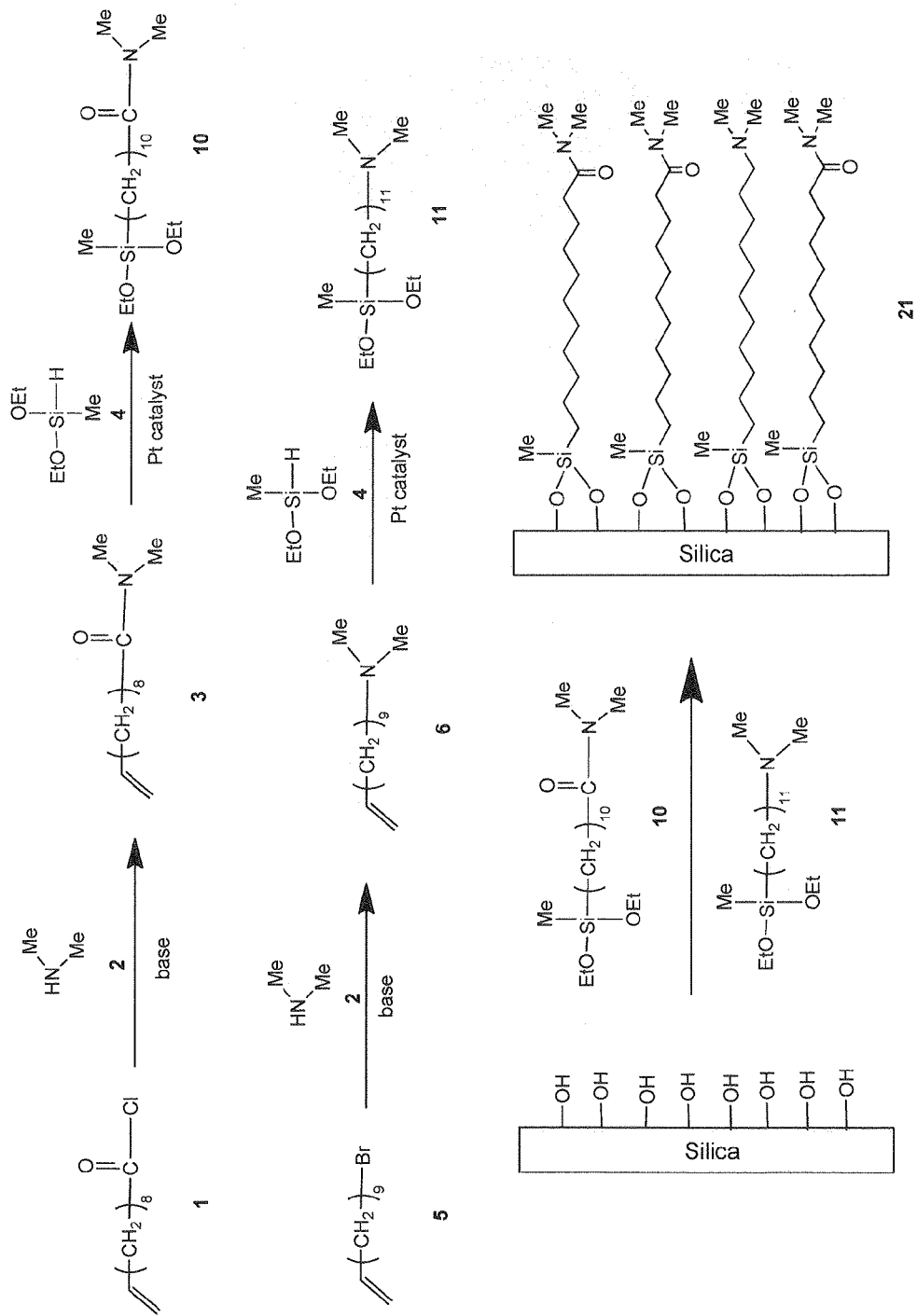
FIG. 7 shows the preparation of WAX/RP mixed-mode media.

Dimethylamine (2) was mixed with an excess of triethylamine (2.0 eq.) in anhydrous $CH_2Cl_2$ and kept between about 0° C. and about 5° C. for 20 min. A solution of 10-undecenoyl chloride (1) (1.0 eq.) in $CH_2Cl_2$ was added drop-wise and the mixture was stirred at ambient temperature for 12 h. The reaction mixture was washed with water, dried over $Na_2SO_4$ and the solvent was removed in vacuo to yield compound 3. Excess methyldiethoxysilane (4) (10 eq.) was added to compound 3 followed by the addition of a solution of catalyst (0.1 mol %), (e.g., hexachloroplatinic acid in a minimum amount of ethanol). After stirring at 50° C. for 24 h, the residual silane and solvent were removed in vacuo to provide compound 10. FIG. 7.

Example 2

Preparation of Compound 11

A 5° C. solution of 11-bromo-1-undecene (5) in THF was added drop-wise to a solution of dimethylamine (2) (10 eq.) in THF and stirred at ambient temperature for 12 h. The volatiles were removed in vacuo and the residue was partitioned between $CH_2Cl_2$ and $H_2O$, dried over $Na_2SO_4$, which was followed by removal of solvent in vacuo to provide compound 6. Excess methyldiethoxysilane (4) (10 eq.) was added to compound 6, followed by the addition of a solution of catalyst (0.1 mol %), hexachloroplatinic acid in a minimum amount of ethanol). After stirring at 50° C. for 24 h, the residual silane and solvent were removed in vacuo to provide silyl compound 11. FIG. 7.

Example 3

Preparation of Phase 21

Compounds 10 and 11 were mixed with a pre-determined ratio in toluene. Then a pre-determined quantity of raw silica gel was added to the solution with stirring until uniformity was obtained. The reaction mixture was kept under reflux for 3 days. The resulting mixture was filtered, washed with acetone, and dried in vacuum oven at 50° C. for 5 h to give functionalized silica of composition 21. An end-capping step using trialkylchloro silane and/or dialkyldichloro silane, may also be incorporated to produce a packing material for chromatographic separations. FIG. 7.

In an exemplary protocol, 18 g of compound 10, 1 g of compound 11 and 15 g of raw silica gel (particle size, 1.9-µm; pore size, 175-Å; surface area, 225 $m^2/g$) were dispersed in 50 mL of toluene (anhydrous) in a 250-mL round bottom flask and mixed in toluene. Then a pre-determined quantity of raw silica gel was added to the solution with stirring until uniformity was obtained. The reaction mixture was mechanically stirred and kept under reflux for 72 h. The resulting mixture was filtered and washed with 200 mL of toluene. The cake was dried in a vacuum oven at ambient temperature for 20 h to give the functionalized silica of Phase 21. Note that an end-capping step using trialkylchloro silane and/or dialkyldichloro silane may also be included.

Example 4

Preparation of Phase 22

Figure 9:
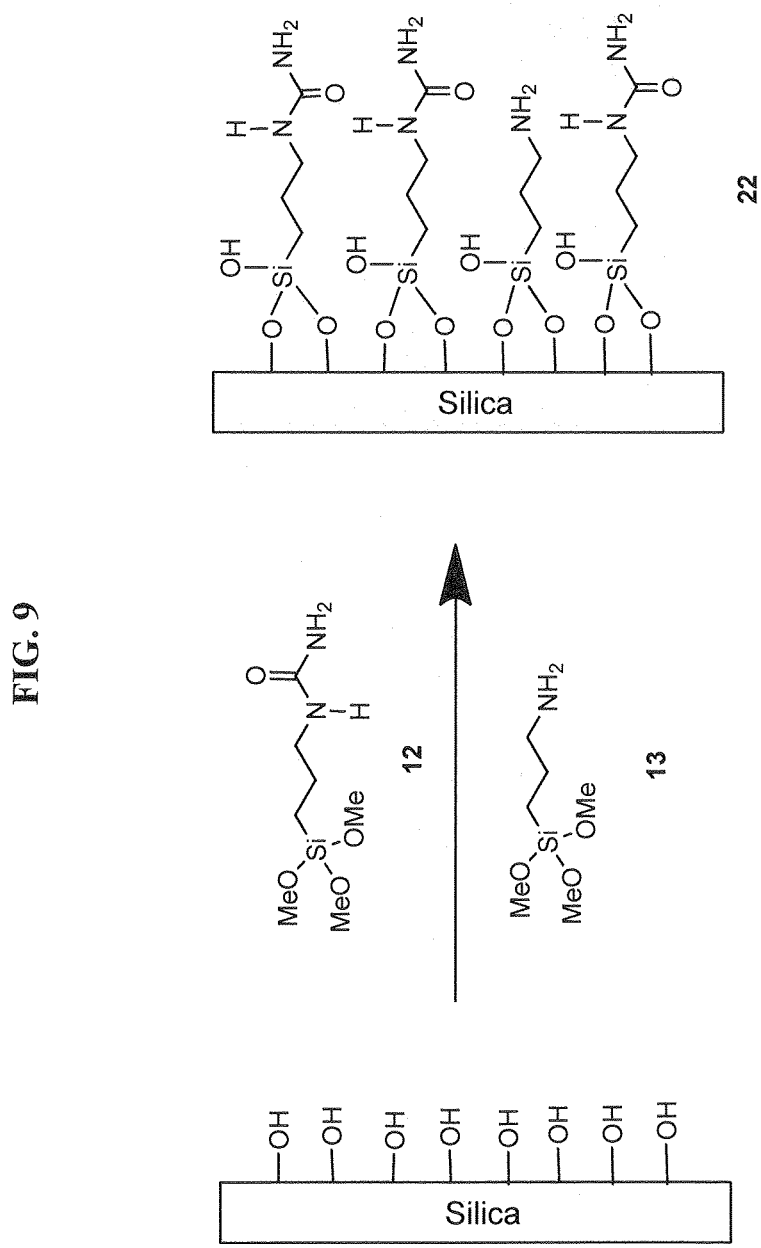
FIG. 9 shows the preparation of WAX/HILIC mixed-mode media

Ureidopropyltrimethoxysilane (12) and 3-aminopropyltrimethoxysilane (13) were mixed in a pre-determined ratio in toluene. Then a pre-determined quantity of raw silica gel was added to the solution with stirring till uniformity. The reaction mixture was kept under reflux for 3 days. The resulting mixture was filtered, washed with acetonitrile, and dried in vacuum oven at 50° C. for 5 h to give functionalized silica of Phase 22. FIG. 9.

In an exemplary protocol, 10 g of ureidopropyltrimethoxysilane (12) and 1 g of 3-aminopropyltrimethoxysilane (13) were mixed in 30 mL toluene (anhydrous). Then 15 g of raw silica gel (particle size, 1.9-µm; pore size, 175-Å; surface area, 225 $m^2/g$) was added to the solution with stirring till uniformity. The reaction mixture was kept under reflux for 2 days. The resulting mixture was filtered, washed with acetonitrile, and dried in vacuum oven at ambient temperature for 20 h to give functionalized silica of Phase 22. FIG. 9.

Example 5

Reverse-Phase/Anion Exchange Mixed Mode Phase

Column Packing

A 2.1 mm (i.d.)×150 mm (length) 316 stainless steel HPLC column housing was packed with Phase 21 for chromatographic evaluation using the high-pressure slurry packing technique.

Mobile Phase Preparation [acetonitrile/100 mM ammonium acetate buffer, pH5=50/50 (v/v)]

Step 1—Placed 7.75±0.03 g ammonium acetate, 2.00±0.01 g acetic acid and 998.0±0.5 g of D.I. water into a 1000-mL eluent bottle. Mixed well by sonication. Step 2—Weighed 500.0±0.2 g of above solution and 391.0±0.5 g acetonitrile into a 1000-mL eluent bottle. Mixed well by sonication. The resulting solution was used as the mobile phase for determination of anion-exchange capacity for the reverse-phase/anion-exchange mixed-mode phase.

Test Probe

The test mixture contained uracil (0.1 mg/mL), octylphenoxyethoxyethyl dimethylbenzyl ammonium chloride (0.1 mg/mL), sodium tosylate (0.2 mg/mL) and propyl benzene (0.4 mg/mL) dissolved in the mobile phase.
Chromatographic Conditions
Column: 1.9-μm particles of Phase 21 packed in 2.1×150-mm format
Mobile Phase Acetonitrile/100 mM ammonium acetate buffer, pH5=50/50 (v/v)
Flow rate: 0.21 mL/min;
Injection volume: 1 μL;
Temperature: 30° C.;
Detection: UV at 220 nm;
Sample: uracil (0.1 mg/mL), octylphenoxyethoxyethyl dimethylbenzyl ammonium chloride (0.1 mg/mL), sodium tosylate (0.2 mg/mL) and propyl benzene (0.4 mg/mL) dissolved in the mobile phase.
The resulting chromatogram is FIG. 8.

Example 6

HILIC/Anion Exchange Mixed Mode Phase

Column Packing
A 2.1 mm (i.d.)×150 mm (length) 316 stainless steel HPLC column housing was packed with Phase 22 for chromatographic evaluation using the high-pressure slurry packing technique.
Mobile Phase Preparation [Acetonitrile/100 mM Ammonium Acetate Buffer, pH5=90/10 (v/v)]
Step 1—Placed 7.75±0.03 g ammonium acetate, 2.00±0.01 g acetic acid and 998.0±0.5 g of D.I. water into a 1000-mL eluent bottle. Mixed well by sonication. Step 2—Weighed 100.0±0.2 g of above solution and 704.0±0.5 g acetonitrile into a 1000-mL eluent bottle. Mixed well by sonication. The resulting solution was used as the mobile phase for determination of anion-exchange capacity for the HILIC/anion-exchange mixed-mode phase.
Test Probe
The test mixture contains acetaminophen, salicylic acid and acetyl salicylic acid (aspirin) dissolved in the mobile phase at the concentration of 0.1 mg/mL. The retention of and acetyl salicylic acid is the indicator of anion-exchange capacity of the phase. The elution order of acetaminophen and acetyl salicylic acid suggests the selectivity.
Chromatographic Conditions
Column: 1.9-μm particles of Phase 22 packed in 2.1×150 mm format
Mobile Phase: acetonitrile/100 mM ammonium acetate buffer, pH 5=90/10 (v/v)
Flow rate: 0.21 mL/min;
Injection volume: 1 μL;
Temperature: 30° C.;
Detection: UV at 220 nm
Sample: Acetaminophen, salicylic acid and acetyl salicylic acid (0.1 mg/mL each in mobile phase).
The resulting chromatogram is FIG. 10.

Example 7

HILIC/Anion Exchange/Cation Exchange Trimodal Phase

Figure 11:
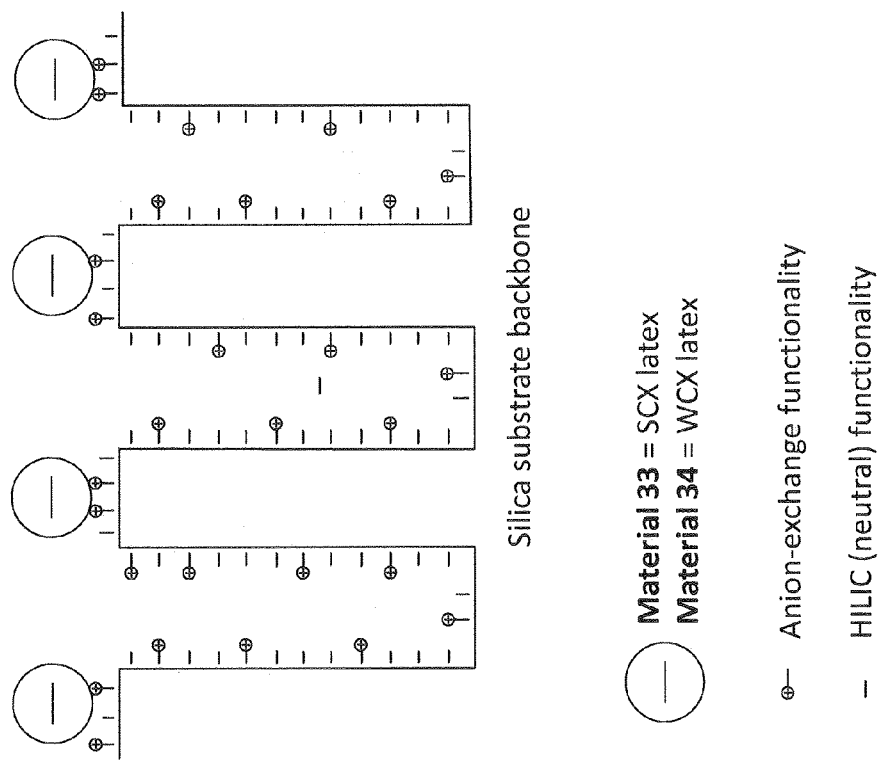
FIG. 11 is a schematic of HILIC/WAX/SCX mixed trimodal media (33) and of HILIC/WAX/WCX mixed trimodal media (34).

Preparation of HILIC/WAX/SCX Trimodal Phase
10 g of Phase 22 was dispersed in 100 mL of ammonium acetate buffer (100 mM, pH5). Separately, 100 mL of sulfonated latex were adjusted to pH 6 with aqueous ammonia and acetic acid. The mixtures of Phase 22 and sulfonated latex were combined and the resulting mixture was stirred at ambient temperature for 3 h. The functionalized silica particles were filtered off and thoroughly washed with D.I. water followed by acetonitrile to give the material 33, as shown in FIG. 11. Thus, material 33 includes a first ion exchange site in the form of a weak anion exchange moiety, an uncharged binding site in the form of a hydrophilic interaction moiety, and a second ion exchange site in the form of a strong cation exchange moiety. The strong cation exchange moieties are from the sulfonated latex.
Preparation of HILIC/WAX/WCX Trimodal Phase
10 g of Phase 22 was dispersed in 100 mL of ammonium acetate buffer (100 mM, pH5). Separately, 100 mL of carboxylated latex were adjusted to pH 6 with aqueous ammonia and acetic acid. The mixtures of Phase 22 and a carboxylated latex were combined and the resulting mixture was stirred at ambient temperature for 3 h. The functionalized silica particles were filtered off and thoroughly washed with D.I. water followed by acetonitrile to give the material 34, as shown in FIG. 11. Thus, material 34 includes a first ion exchange site in the form of a weak anion exchange moiety, an uncharged binding site in the form of a hydrophilic interaction moiety, and a second ion exchange site in the form of a weak cation exchange moiety. The weak cation exchange moieties are from the carboxylated latex.
The latex was synthesized according to the procedure set forth in commonly-owned copending United States Pre-Grant Publication No. 2009/0277838A1.

Example 8

Figure 3A:
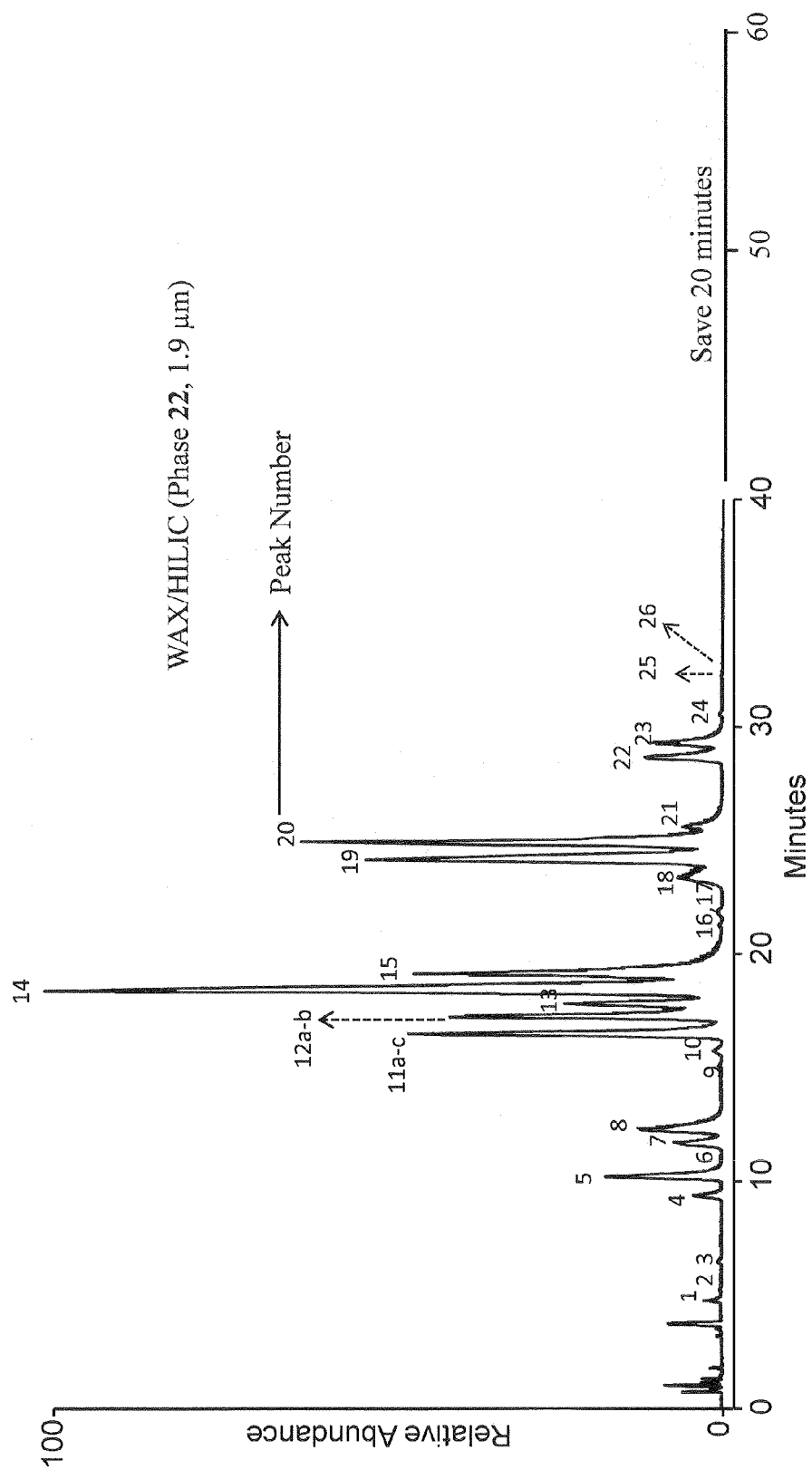
FIGS. 3A & 3B are chromatograms showing a comparative separation of 2AB-linked N-glycans from bovine fetuin by two different columns. All the peaks for both the columns are detected by MS detection in negative mode with mass scan range 400-2200 Dalton. A. Chromatographic analysis in a WAX/HILIC (Phase 22, 1.9 μm) column, B. Chromatographic analysis in a commercial amide HILIC column (1.7 μm). The WAX/HILIC (Phase 22, 1.9 μm) column provides superior separation in terms of selectivity based on charge, size, polarity and resolution based on the peak width to the 1.7 μm commercial amide HILIC column. The gradient conditions for separation are provided in the examples section. The list of glycans identified in bovine fetuin is shown in Table 7.

HILIC/Anion Exchange Mixed Mode Phase for Fluorescent Group Labeled N-Glycan Separation FIG. 1 is a chromatogram of the separation of 2AB-linked N-glycans from bovine fetuin. The glycans were detected by fluorescence detection. FIG. 2 shows the separation of 2AA-linked N-glycans from Human IgG polyclonal antibody using the WAX/HILIC (Phase 22, 1.9 μm) column detected by both fluorescence and MS detection method. A volatile mobile phase containing ammonium formate, water and acetonitrile was used (as shown in Table 3 of Example 9 below) thus the resulting method is compatible with mass spectroscopy. Table 1 provides a list of glycan structure present in 2AA-linked N-glycans isolated from Human IgG. The selectivity and resolution of separation of each peak and peak separation based on charge are unique as compared to the commercial column used in FIG. 3B. The peaks width and peak resolution are highly comparable with commercial glycan columns (based on 1.7 μm substrate particle). Referring to FIG. 3A, the chromatogram using the WAX/HILIC (Phase 22, 1.9 μm) column provides faster separation (e.g., about 40 min) as compared to the commercial glycan column. Table 7 (provided in Example 9 below) provides a list of glycan structure present in 2AB-linked N-glycans isolated from Bovine fetuin. The commercial column doesn't provide separation based on charge, which makes characterizing minute quantity of different charge state glycans because those species are co-eluted with other major peaks in commercial columns.

TABLE 1

Structural characterization of glycans present in each peak by
the separation of 2AA labeled N-glycans from human IgG
using the WAX/HILIC (Phase 22, 1.9 μm) column.

| Peak No. | Glycan Structure (2-AA label not shown) | Charge of glycan (without 2AA label) | Molecular Mass (including 2AA label) |
|---|---|---|---|
| 1 | | 0 | 1380.5178 |
| 2 | | 0 | 1437.5393 |
| 3 | | 0 | 1583.5972 |
| 4 | | 0 | 1542.5706 |
| 5 | | 0 | 1542.5706 |
| 6 | | 0 | 1786.6766 |
| 6 | | 0 | 1599.5921 |

TABLE 1-continued

Structural characterization of glycans present in each peak by the separation of 2AA labeled N-glycans from human IgG using the WAX/HILIC (Phase 22, 1.9 μm) column.

| Peak No. | Glycan Structure (2-AA label not shown) | Charge of glycan (without 2AA label) | Molecular Mass (including 2AA label) |
|---|---|---|---|
| 7 | | 0 | 1745.6500 |
| 8 | | 0 | 1745.6500 |
| 9 | Unknown | | Unknown |
| 10 | | 0 | 1761.6449 |
| 11 | | 0 | 1907.7028 |
| 12 | | 0 | 2110.7822 |
| 13 | | −1 | 2036.7454 |
| | | −1 | 2052.7404 |

TABLE 1-continued

Structural characterization of glycans present in each peak by the separation of 2AA labeled N-glycans from human IgG using the WAX/HILIC (Phase 22, 1.9 μm) column.

| Peak No. | Glycan Structure (2-AA label not shown) | Charge of glycan (without 2AA label) | Molecular Mass (including 2AA label) |
|---|---|---|---|
| 14 | | −1 | 2036.7454 |
| 15 | | −1 | 2052.7404 |
| 16 | | −1 | 2198.7983 |
| 17 | | −1 | 2401.8776 |

■ N-acetyl Glucosamine (GlcNAc)

● Mannose (Man)

○ Galactose (Gal)

◆ N-Acetyl Neuraminic Acid (Neu5Ac)

◇ N-Glycolyl Neuraminic Acid (Neu5Gc)

▲ L-Fucose (L-Fuc)

Example 9

HILIC/Anion Exchange Mixed Mode Phase for Unlabeled O- and N-Glycan Separation FIG. 4 is a chromatogram of the separation of unlabeled N-glycans from bovine fetuin using a WAX/HILIC (Phase 22, 1.9 μm) column. The glycans were detected by MS detection. The eluents and gradient conditions are same as the gradient conditions (shown below) for a fluorescent group labeled N-glycan separation using ammonium formate (0-100 mM), water and acetonitrile) as eluent. As shown in FIG. 4, unlabeled glycans are separated based on charge, size, and polarity. All the peaks are detected by MS detector and listed in Table 2. The glycan profiles and quantity of higher sialic acid linked glycans are different from the profiling of a fluorescent group labeled glycans. The change of glycan profiles in terms of qualitative and quantitative amount of each charge state and individual glycans during fluorescent group labeling was observed. Separated unlabeled glycans also provided enough MS/MS fragmentation for the characterization of glycans present in each peak. MS/MS fragmentation of labeled glycans requires less sample compared to the amount required for unlabeled glycans. Thus, the WAX/HILIC (Phase 22, 1.9 μm) column is useful for the analysis of both unlabeled and labeled N-glycans depending on the amount of sample available. If the sample amount is not a concern, then analysis of unlabeled glycan using a WAX/HILIC (Phase 22, 1.9 µm) column is a suitable strategy to determine the native structure without modification by labeling. O-glycans are released by reductive chemical digestion methods, which provide reduced forms of O-glycans from proteins and mucins. Fluorescent labeling of O-glycans is challenging because the released glycans lack a reaction aldehyde group at the C1 position of the glycans. O-glycans are also a mixture of sialic acid linked charged glycans and neutral glycans. Thus, the WAX/HILIC (Phase 22, 1.9 µm) column is an ideal column for the separation of O-glycans and detection by mass spectrometry.

TABLE 2

Structural characterization of glycans present in each peak by the separation of reduced unlabeled N-glycans from Bovine fetuin using the WAX/HILIC (Phase 22, 1.9 µm) column.

| Peak No. | Compound Structure | Charge for glycans | Molecular Mass (Reduced glycans) |
|---|---|---|---|
| 1 | 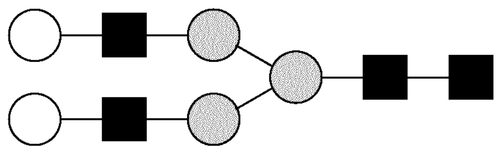 | 0 | 1642.6078 |
| 2 | 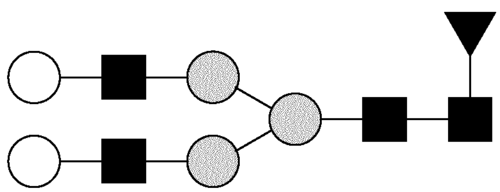 | 0 | 1788.6657 |
| 3 | 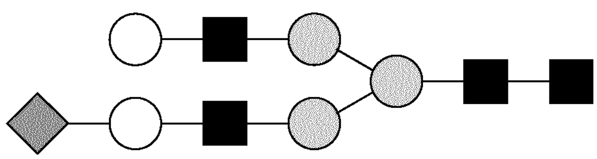 | −1 | 1933.7032 |
| 4 | 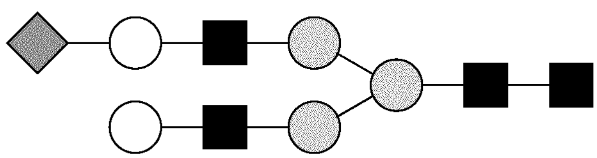 | −1 | 1933.7032 |
| 5 | 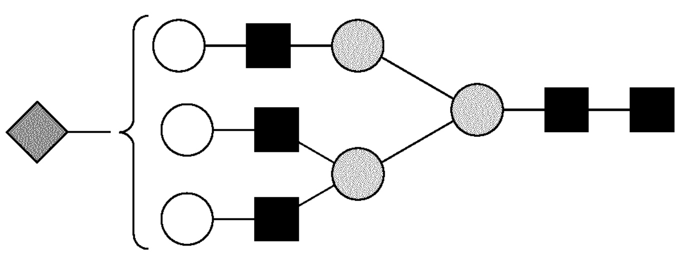 | −1 | 2298.8354 |
| 6 | Unknown | Unknown | Unknown |
| 7 | 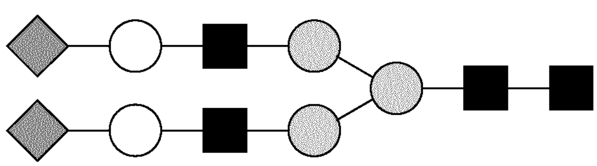 | −2 | 2224.7987 |

TABLE 2-continued

Structural characterization of glycans present in each peak by the separation of reduced unlabeled N-glycans from Bovine fetuin using the WAX/HILIC (Phase 22, 1.9 µm) column.

| Peak No. | Compound Structure | Charge for glycans | Molecular Mass (Reduced glycans) |
|---|---|---|---|
| 8a | 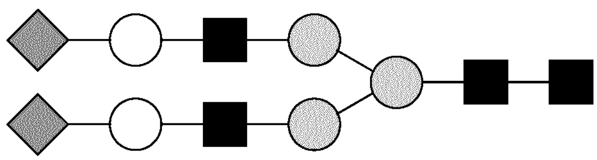 | −2 | 2224.7987 |
| 8b | 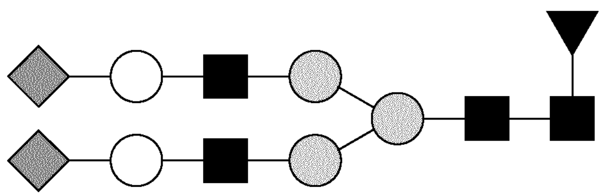 | −2 | 2370.8566 |
| 8c | 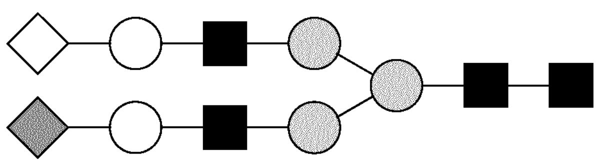 | −2 | 2240.7936 |
| 9a | 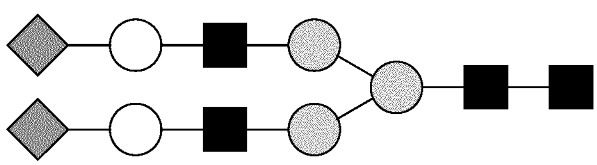 | −2 | 2224.7987 |
| 9b | 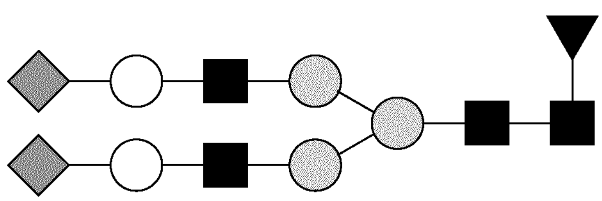 | −2 | 2370.8566 |
| 9c | 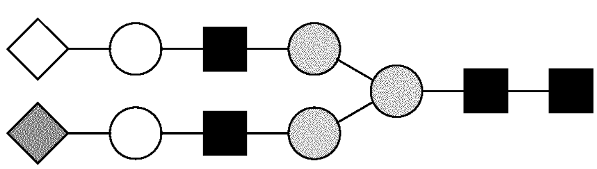 | −2 | 2240.7936 |
| 10a | 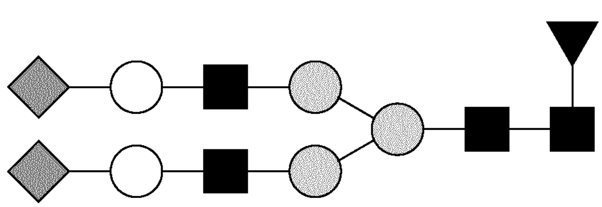 | −2 | 2370.8566 |

US 9,169,331 B2
TABLE 2-continued
Structural characterization of glycans present in each peak by
the separation of reduced unlabeled N-glycans from Bovine fetuin
using the WAX/HILIC (Phase 22, 1.9 μm) column.
| Peak No. | Compound Structure | Charge for glycans | Molecular Mass (Reduced glycans) |
|---|---|---|---|
| 10b | 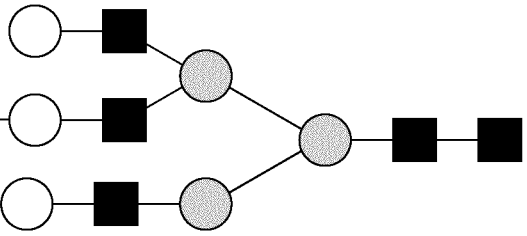 | −2 | 2589.9309 |
| 10c | 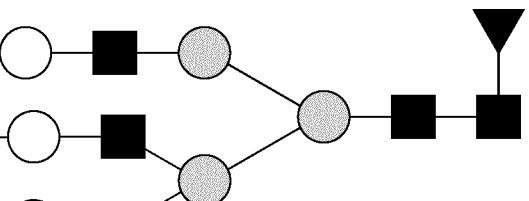 | −2 | 2735.9888 |
| 11a | 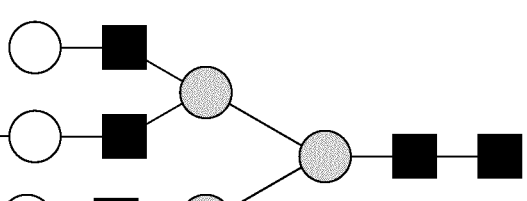 | −2 | 2589.9309 |
| 11b | 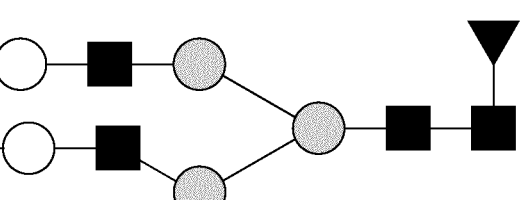 | −2 | 2735.9888 |
| 12 | 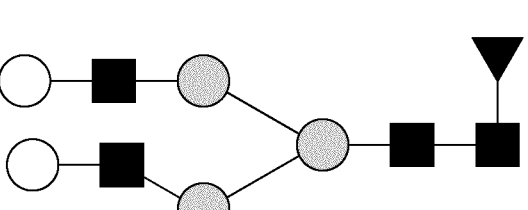 | −2 | 2735.9888 |

TABLE 2-continued

Structural characterization of glycans present in each peak by
the separation of reduced unlabeled N-glycans from Bovine fetuin
using the WAX/HILIC (Phase 22, 1.9 μm) column.

| Peak No. | Compound Structure | Charge for glycans | Molecular Mass (Reduced glycans) |
|---|---|---|---|
| 13 | 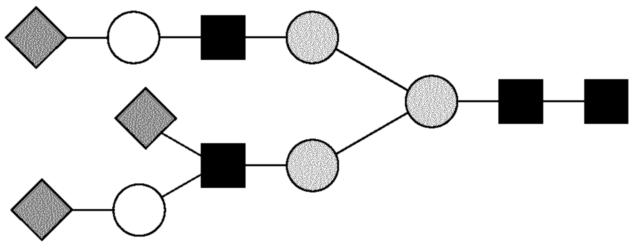 | −3 | 2515.8941 |
| 14 | 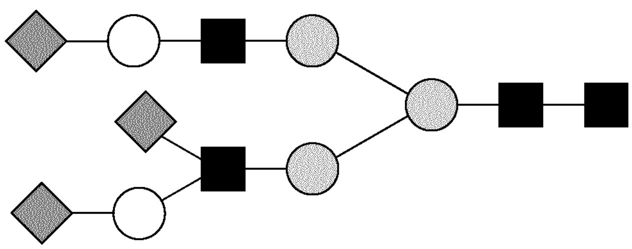 | −3 | 2515.8941 |
| 15 | 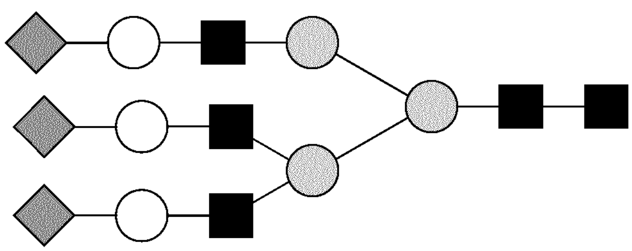 | −3 | 2881.0263 |
| 16 | 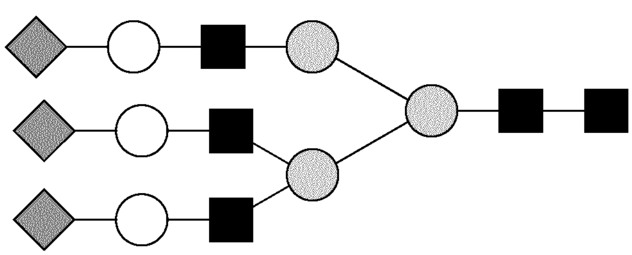 | −3 | 2881.0263 |
| 17 | 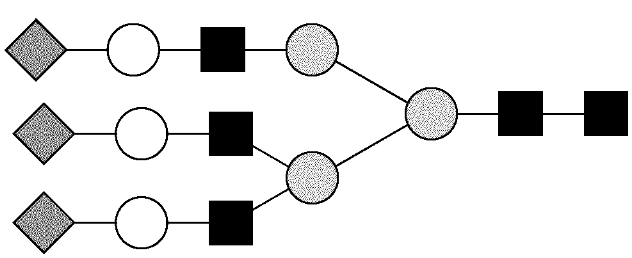 | −3 | 2881.0263 |

TABLE 2-continued

Structural characterization of glycans present in each peak by
the separation of reduced unlabeled N-glycans from Bovine fetuin
using the WAX/HILIC (Phase 22, 1.9 μm) column.

| Peak No. | Compound Structure | Charge for glycans | Molecular Mass (Reduced glycans) |
|---|---|---|---|
| 18 | 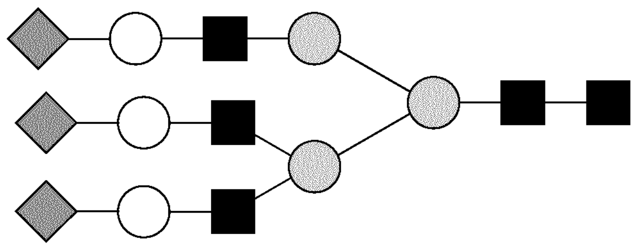 | −3 | 2881.0263 |
| 19 | 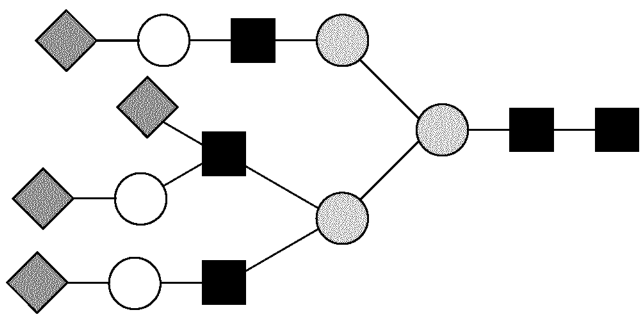 | −4 | 3172.1217 |
| 20 | 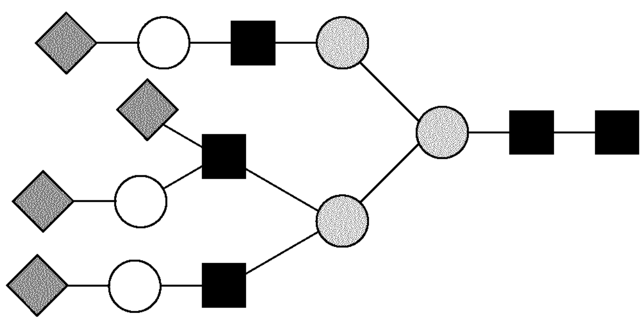 | −4 | 3172.1217 |
| 21 | 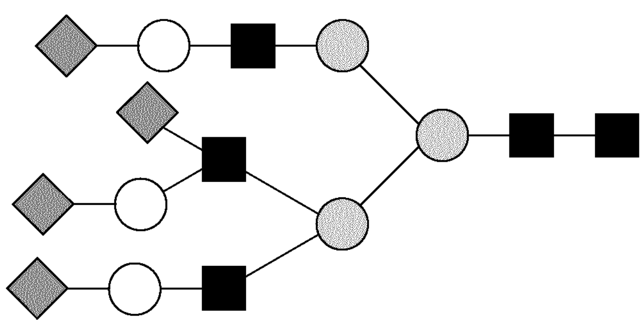 | −4 | 3172.1217 |

TABLE 2-continued

Structural characterization of glycans present in each peak by
the separation of reduced unlabeled N-glycans from Bovine fetuin
using the WAX/HILIC (Phase 22, 1.9 μm) column.

| Peak No. | Compound Structure | Charge for glycans | Molecular Mass (Reduced glycans) |
|---|---|---|---|
| 22 | 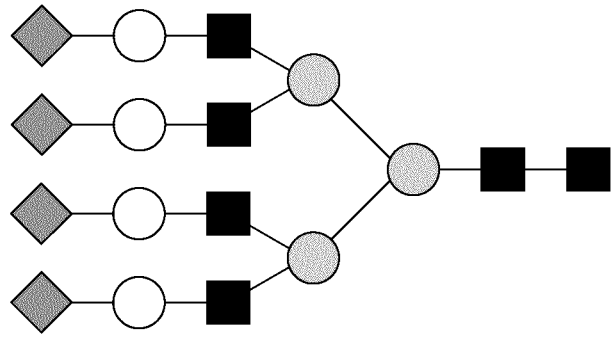 | −4 | 3537.2539 |
| 23 | 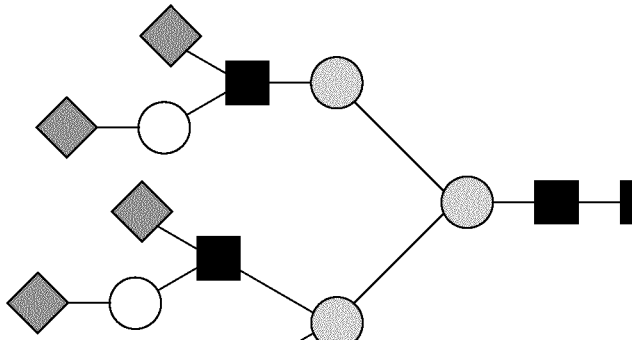 | −5 | 3463.2171 |
| 24 | 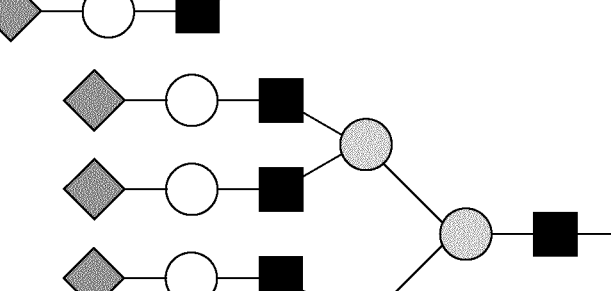 | −5 | 3824.3493 |

■ N-acetyl Glucosamine (GlcNAc)

● Mannose (Man)

○ Galactose (Gal)

◆ N-Acetyl Neuraminic Acid (Neu5Ac)

◇ N-Glycolyl Neuraminic Acid (Neu5Gc)

▲ L-Fucose (L-Fuc)

Experimental conditions for the separation of N-glycans from labeled bovine fetuin by WAX/HILIC (Phase 22, 1.9 µm) column for FIG. 1: Ternary gradient conditions:
Column: Phase 22, 1.9 µm
Dimension: 2.1×150 mm
Mobile phase: A—Acetonitrile; B—water; C—Ammonium formate (100 mM, pH=4.4)
Flow: 0.4 mL/min
Temp: 30° C.
Injection: 50 pmole
Detection: Fluorescence (FLD3400)
Sample: 2AB-N-glycan from bovine fetuin

TABLE 3

Gradient conditions for the separation of 2AB-N-glycans from bovine fetuin using a WAX/HILIC (Phase 22, 1.9 µm) column.

| Time (min) | % A | % B | % C | Flow (mL/min) | Curve |
|---|---|---|---|---|---|
| −10 | 78 | 20 | 2 | 0.4 | 5 |
| 0 | 78 | 20 | 2 | 0.4 | 5 |
| 30 | 70 | 20 | 10 | 0.4 | 5 |
| 35 | 60 | 20 | 20 | 0.4 | 5 |
| 40 | 50 | 20 | 30 | 0.4 | 5 |

Experimental conditions for the separation of N-glycans from labeled and unlabeled bovine fetuin on a WAX/HILIC (Phase 22, 1.9 µm) column for FIG. 3A and FIG. 4: Binary gradient conditions
Column: Phase 22, 1.9
Mobile phase: A: 80% Acetonitrile+20% water
B: Ammonium formate (80 mM, pH=4.4)
Flow: 0.4 mL/min
Temp: 30° C.
Detection: Fluorescence (FLD3400) and MS detector
MS Instrument: Q-Exactive (Thermo Scientific, San Jose, Calif.)
MS mode: Negative
Default charge state: 2
FT-MS (Full MS)
  Micro scans: 1
  Resolution: 70,000
  Scan range: m/z=380-2200
MS/MS (MS2)
  Micro scans: 1
  Resolution: 17,500
FT-MS range: m/z=400-2200
Injection: 50 pmole for 2AB-linked N-glycans from bovine fetuin; 500 pmole for unlabeled N-glycans from bovine fetuin
Sample: Unlabeled and 2AB labeled —N-glycan from bovine fetuin

TABLE 4

Gradient conditions for the separation of N-glycans from bovine fetuin using a WAX/HILIC (Phase 22, 1.9 µm) column.

| Time (min) | % A | % B | Flow (mL/min) | Curve |
|---|---|---|---|---|
| −10 | 97.5 | 2.5 | 0.4 | 5 |
| 0 | 97.5 | 2.5 | 0.4 | 5 |
| 30 | 87.5 | 12.5 | 0.4 | 5 |
| 35 | 75.0 | 25.0 | 0.4 | 5 |
| 40 | 62.5 | 37.5 | 0.4 | 5 |

Experimental conditions for the separation of 2AA linked N-glycans from human IgG on a WAX/HILIC (Phase 22, 1.9 µm) column (FIG. 2A and FIG. 2B): Binary gradient conditions.
Column: Phase 22, 1.9 µm
Mobile phase: A: 80% Acetonitrile+20% water
  B: Ammonium formate (80 mM, pH=4.4)
Flow: 0.4 mL/min
Temp: 30° C.
Detection: Fluorescence (FLD3400) and MS detector
MS Instrument: Q-Exactive
MS mode: Negative
FT-MS range: m/z=400-2200
Injection: 50 µmole
Sample: 2AA-N-glycan from human IgG

TABLE 5

Gradient conditions for the separation of 2AA N-glycans from human IgG using WAX/HILIC (Phase 22, 1.9 µm) column.

| Time (min) | % A | % B | Flow (mL/min) | Curve |
|---|---|---|---|---|
| −10 | 99 | 1 | 0.4 | 5 |
| 0 | 99 | 1 | 0.4 | 5 |
| 30 | 87.5 | 12.5 | 0.4 | 5 |
| 35 | 75.0 | 25.0 | 0.4 | 5 |

Figure 3B:
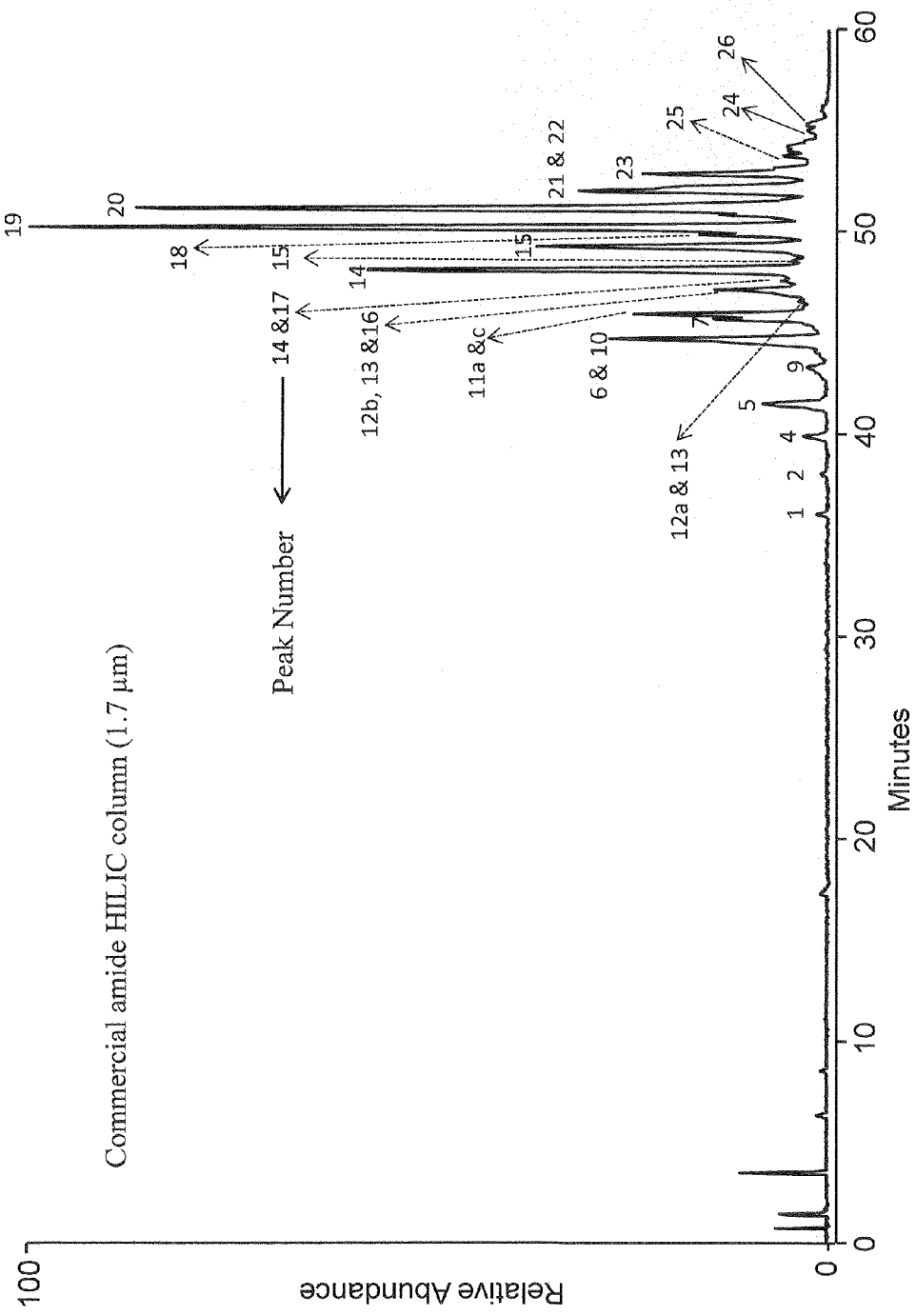

Experimental conditions for the separation of 2AB linked N-glycans from bovine fetuin on a commercial amide HILIC column (1.7 µm) (FIG. 3B). It should be noted that the glycan separation using the WAX/HILIC column of FIG. 3A was much faster than the chromatogram using the commercial amide HILIC column of FIG. 3B in that it was about 20 minutes faster. In addition, the WAX/HILIC column of FIG. 3A eluted glycans sequentially based on the magnitude of the native charge and the commercial amide HILIC column of FIG. 3B did not. For instance, the commercial amide HILIC column of FIG. 3B eluted peak 9 with a negative 2 charge followed by peak 6 with a negative 1 charge, and then peak 11a with a negative 2 charge.
Mobile phase: A: Acetonitrile
  B: Ammonium formate (100 mM, pH=4.4)
Flow: 0.4 mL/min
Temp: 30° C.
Detection: MS detector
MS Instrument: Q-Exactive
MS mode: Negative
FT-MS range: m/z=400-2200
Injection: 50 pmole
Sample: 2AB-N-glycan from bovine fetuin

TABLE 6

Gradient conditions for the separation of 2AB N-glycans from bovine fetuin using a commercial amide HILIC column (1.7 µm)

| Time (min) | % A | % B | Flow (mL/min) | Curve |
|---|---|---|---|---|
| −10 | 75.0 | 25.0 | 0.4 | 5 |
| 0 | 75.0 | 25.0 | 0.4 | 5 |
| 5 | 75 | 25 | 0.4 | 6 |
| 55 | 55 | 45 | 0.4 | 6 |
| 63 | 50 | 50 | 0.4 | 6 |

TABLE 7

Structural characterization of glycans present in each peak by the separation of 2AB-labeled N-glycans from bovine fetuin using the WAX/HILIC (Phase 22, 1.9 μm) column.

| Peak No. | Compound Structure (2AB label not shown) | Charge for glycans (without 2AB label) | Molecular Mass (including 2AB label) |
|---|---|---|---|
| 1 | | 0 | 1760.6609 |
| 2 | | 0 | 1906.7188 |
| Unknown | Unknown | Unknown | Unknown |
| 4 | | −1 | 2051.7563 |
| 5 | | −1 | 2051.7563 |
| 6 | | −1 | 2416.8885 |
| 7 | | −1 | 2416.8885 |

TABLE 7-continued

Structural characterization of glycans present in each peak by the separation of 2AB-labeled N-glycans from bovine fetuin using the WAX/HILIC (Phase 22, 1.9 μm) column.

| Peak No. | Compound Structure (2AB label not shown) | Charge for glycans (without 2AB label) | Molecular Mass (including 2AB label) |
|---|---|---|---|
| 8 | | −1 | 2416.8885 |
| 9 | | −2 | 2342.8518 |
| 10 | | −2 | 2342.8518 |
| 11a | | −2 | 2342.8518 |
| 11b | | −2 | 2488.9097 |
| 11c | | −2 | 2358.8467 |
| 12a | | −2 | 2342.8518 |
| 12b | | −2 | 2358.8467 |

TABLE 7-continued

Structural characterization of glycans present in each peak by the separation of 2AB-labeled N-glycans from bovine fetuin using the WAX/HILIC (Phase 22, 1.9 μm) column.

| Peak No. | Compound Structure (2AB label not shown) | Charge for glycans (without 2AB label) | Molecular Mass (including 2AB label) |
|---|---|---|---|
| 13 | | −3 | 2707.9839 |
| 14 | | −3 | 2707.9839 |
| 15 | | −3 | 2707.9839 |
| 16 | | −3 | 2633.9472 |

TABLE 7-continued

Structural characterization of glycans present in each peak by the separation of 2AB-labeled N-glycans from bovine fetuin using the WAX/HILIC (Phase 22, 1.9 μm) column.

| Peak No. | Compound Structure (2AB label not shown) | Charge for glycans (without 2AB label) | Molecular Mass (including 2AB label) |
|---|---|---|---|
| 17 | | −3 | 2633.9472 |
| 18 | | −3 | 2999.0794 |
| 19 | | −3 | 2999.0794 |
| 20 | | −3 | 2999.0794 |
| 21 | | −3 | 2999.0794 |

TABLE 7-continued
Structural characterization of glycans present in each peak by
the separation of 2AB-labeled N-glycans from bovine fetuin
using the WAX/HILIC (Phase 22, 1.9 μm) column.
| Peak No. | Compound Structure (2AB label not shown) | Charge for glycans (without 2AB label) | Molecular Mass (including 2AB label) |
|---|---|---|---|
| 22 | 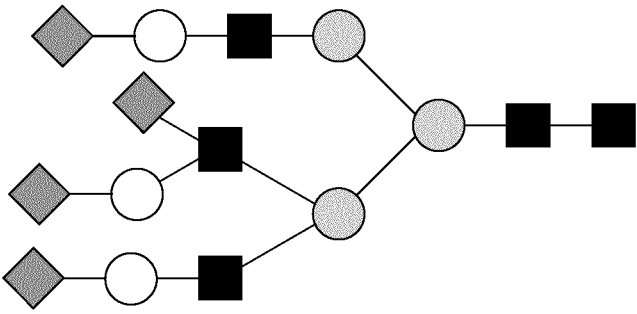 | −4 | 3290.1748 |
| 23 | 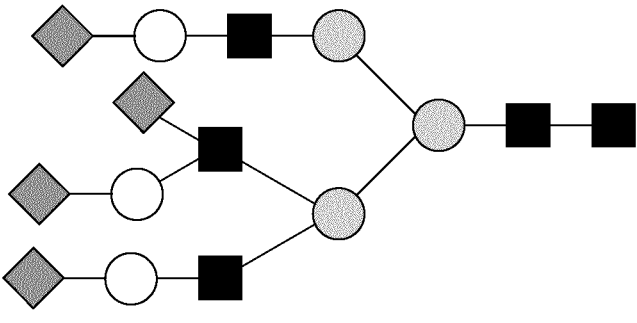 | −4 | 3290.1748 |
| 24 | 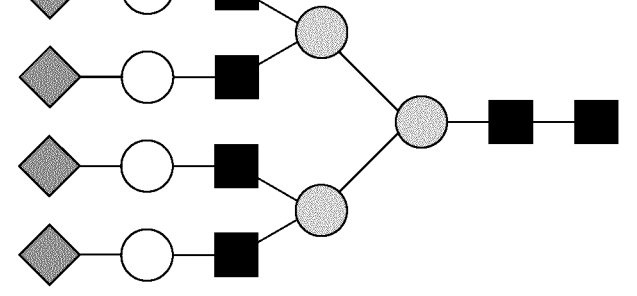 | −4 | 3655.3070 |
| 25 | 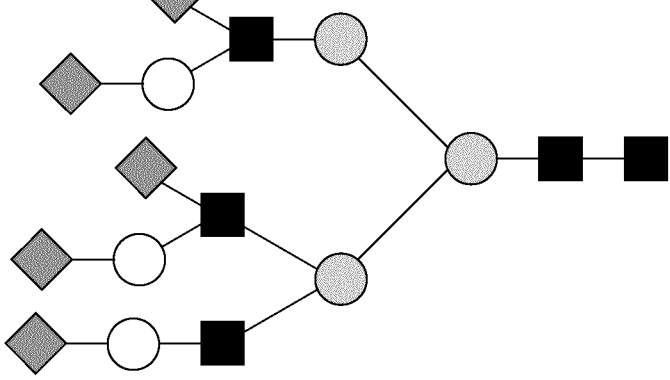 | −5 | 3581.2702 |

TABLE 7-continued

Structural characterization of glycans present in each peak by the separation of 2AB-labeled N-glycans from bovine fetuin using the WAX/HILIC (Phase 22, 1.9 μm) column.

| Peak No. | Compound Structure (2AB label not shown) | Charge for glycans (without 2AB label) | Molecular Mass (including 2AB label) |
|---|---|---|---|
| 26 | | −5 | 3946.4024 |

N-acetyl Glucosamine (GlcNAc)

Mannose (Man)

Galactose (Gal)

N-Acetyl Neuraminic Acid (Neu5Ac)

N-Glycolyl Neuraminic Acid (Neu5Gc)

L-Fucose (L-Fuc)

Example 10

WAX/RP Mixed Mode Phase for Fluorescently Labeled N-Glycan Separation

FIG. 5 is a chromatogram of the separation of 2AB-linked N-glycans from bovine fetuin using a WAX/RP (Phase 21, 1.9 μm) columns. The glycans were detected by fluorescence detection. The eluents (ammonium formate (0-100 mm), water and acetonitrile) used for the separation of glycans are highly compatible with mass spectroscopy. The WAX/RP column operates from low organic to high organic solvent conditions. As shown in FIG. 4, the WAX/RP (Phase 21, 1.9 μm) column separates based on charge, size, isomers and polarity. The number of peaks observed is comparatively higher than other commercial columns and also higher than mixed-mode column (Phase 22, 1.9 μm). This WAX/RP column provides a greater number of peaks for N-glycans from bovine fetuin than commercial columns. This HPLC column provides a high number of detectable peaks (~44) by fluorescence detection. In addition, the WAX/RP column provides a higher peak resolution than the commercial column. The gradient and experimental conditions are shown as follows.

Chromatographic Condition
Column: Phase 21, 1.9 μm
Dimension: 2.1×150 mm
Mobile phase: A: Acetonitrile
  B: Ammonium formate (100 mM, pH=4.4)
  C: Water
Flow: 0.4 mL/min
Temp: 30° C.
Injection: 100 μmole
Detection: Fluorescence (FLD3400)
Sample: 2AB-N-glycan from bovine fetuin

TABLE 8

Gradient conditions for the separation of 2AB N-glycans from bovine fetuin using the WAX/RP (Phase 21, 1.9 μm) column

| Time (min) | % A | % B | % C | Flow (mL/min) |
|---|---|---|---|---|
| −5.0 | 0.0 | 5.0 | 95.0 | 0.4 |
| 0.0 | 0.0 | 5.0 | 95.0 | 0.4 |
| 20.0 | 4.0 | 18.0 | 78.0 | 0.4 |
| 24.0 | 0.7 | 30.0 | 69.3 | 0.4 |
| 44.0 | 6.0 | 30.0 | 64.0 | 0.4 |
| 60.0 | 15.0 | 30.0 | 55.0 | 0.4 |

Example 11

Figure 6:
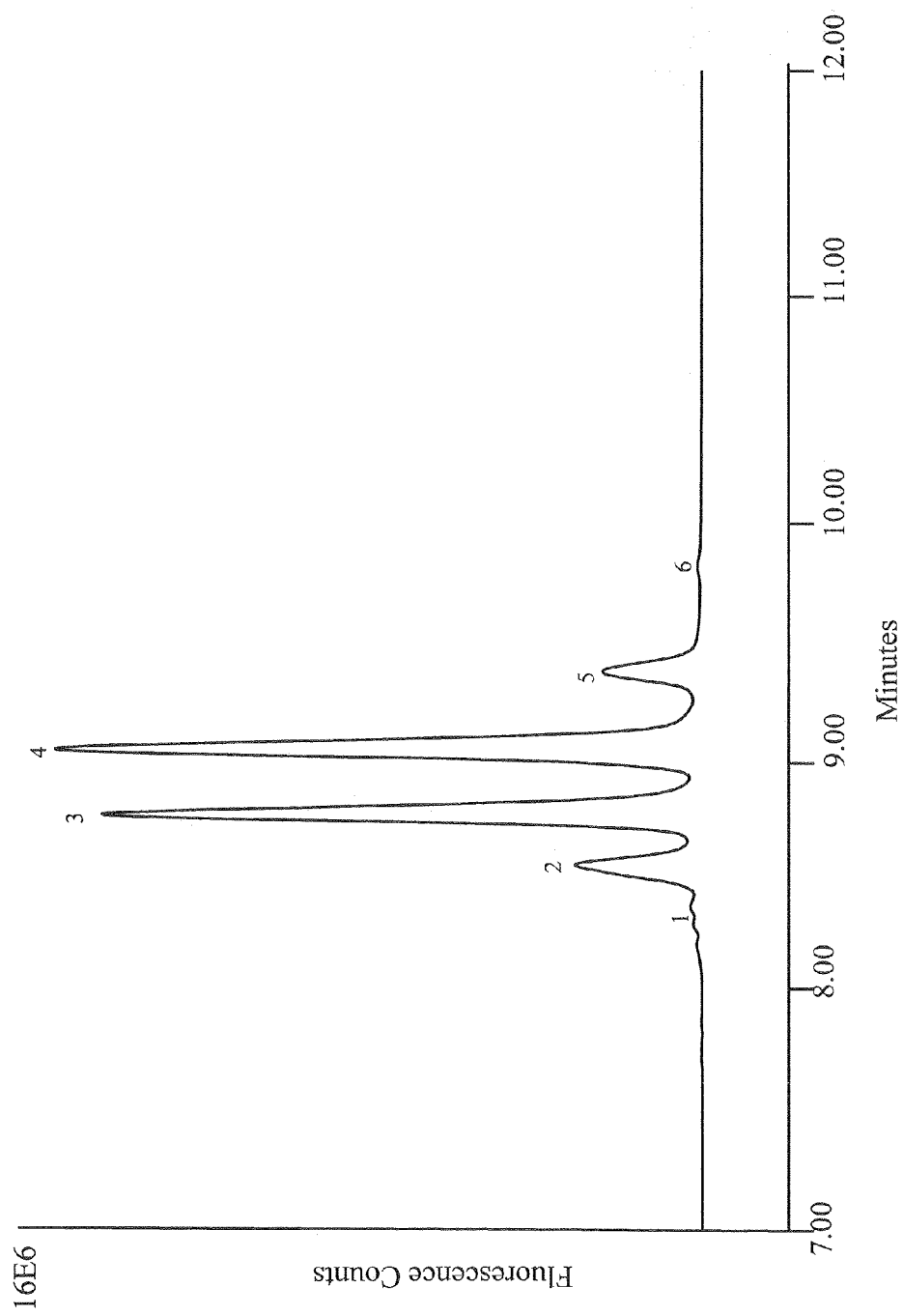
FIG. 6 is a chromatogram showing a separation of 2AB-labeled N-glycans from bovine fetuin using a WAX/HILIC (Phase 22, 1.9 μm) column using a one step gradient condition. The mobile phase has a higher aqueous proportion than that used in FIG. 1 causing all of the glycans having a common charge to coalesce together as a single peak and allowing easy and accurate quantitation for each of the charge states. The peaks were detected by fluorescence detection. Quantitation for each charge state glycan was determined from the comparative area under curve (AUC) for each peak (Table 10).

HILIC/Anion Exchange Mixed Mode Phase for Quantitative Analysis of Labeled N-Glycans from Proteins Based on Charge FIG. 6 shows the separation profile of 2AB-labeled N-glycans from bovine fetuin based on charge or number of sialic acid in the oligosaccharides) on a WAX/HILIC (Phase 22, 1.9 μm) column. In contrast to Example 9, the mobile phase had a single step gradient and a relatively higher aqueous proportion with respect to the organic solvent. The relatively high aqueous proportion caused the HILIC interactions to be attenuated and the chromatographic interactions based on polarity (degree of hydrophilicity) and size to be increased.

As a result of the decreased HILIC interactions, the glycan peak groups that shared a common charge, as illustrated in FIG. 1, coalesced together, as illustrated in FIG. 6. All glycans of the same charge elute together as a single peak. Thus, the glycan quantity can be easily and accurately determined, as shown in Table 10. In addition, the WAX/HILIC (Phase 22) phases are useful for the quantification of unlabeled N- and O-glycans by MS detection.

Chromatographic Conditions for FIG. 6.
Column: Phase 22, 1.9 μm
Dimension: 2.1×150 mm
Mobile phase: A: Acetonitrile
  B: Ammonium formate (50 mM, pH=4.4)
  C: Water
Flow: 0.4 mL/min
Temp: 30° C.
Injection: 50 pmole
Detection: Fluorescence (FLD3400)
Sample: 2AB-N-glycan from bovine fetuin

TABLE 9

Gradient conditions for the quantitative separation of 2AB N-glycans from bovine fetuin using a WAX/HILIC (Phase 22, 1.9 μm) columns

| Time (min) | % A | % B | % C | Flow (mL/min) |
|---|---|---|---|---|
| −5.0 | 90 | 10 | 0 | 0.4 |
| 0.0 | 90 | 10 | 0 | 0.4 |
| 6 | 50 | 20 | 30 | 0.4 |
| 12 | 50 | 20 | 30 | 0.4 |

TABLE 10

Quantitative amounts of each charge state glycans of the 2AB-N-glycans from bovine fetuin using a WAX/HILIC (Phase 22, 1.9 μm) column. The quantitative data corresponds to the peaks of FIG. 6.

| Peak No. | Glycan Type | % AUC from Total |
|---|---|---|
| 1 | Neutral | 0.4 |
| 2 | Mono-sialic | 8.6 |
| 3 | Di-sialic | 38.4 |
| 4 | Tri-sialic | 45.4 |
| 5 | Tetra-sialic | 7.0 |
| 6 | Penta-sialic | 0.2 |

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All publications, patents, and patent applications cited herein are hereby incorporated by reference in their entirety for all purposes.

What is claimed is:

1. A multimodal chromatographic method of separating a first glycan component from a second glycan component of a glycan mixture, said method comprising:

(a) contacting said glycan mixture with a multimodal chromatographic medium comprising an ion exchange chromatographic moiety bound to a first substrate and a urea hydrophilic interaction chromatographic moiety-bound to a second substrate, and an aqueous eluent comprising an electrolyte and an organic solvent under conditions effective to achieve said separating, thereby separating said first glycan component and said second glycan component.

2. The method according to claim 1, wherein said ion exchange chromatographic moiety is an anion exchange moiety.

3. The method according to claim 2, wherein said ion exchange moiety is an amine.

4. The method according to claim 1, wherein said ion exchange chromatographic moiety is bound to said first substrate through a first linker.

5. The method according to claim 4 wherein said urea hydrophilic interaction chromatographic moiety is bound to said second substrate through a second linker.

6. The method of claim 5, wherein a member selected from said first linker moiety, said second linker moiety and a combination thereof is a substituted or unsubstituted alkyl moiety.

7. The method of claim 6, wherein said substituted or unsubstituted alkyl linker is from about 3 carbons to about 40 carbons in length.

8. The method according to claim 7, wherein said first linker is from about 3 carbons to about 30 carbons in length.

9. The method according to claim 7, wherein said second linker is from about 8 carbons to about 40 carbons in length.

10. The method according to claim 5, wherein said first substrate and said second substrate are the same substrate.

11. The method according to claim 5, wherein said first substrate and said second substrate are different substrates.

12. The method according to claim 8, wherein said ion exchange chromatographic moiety together with said first linker has the formula:

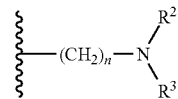

wherein
R² and R³ are independently selected from H, substituted or unsubstituted alkyl and substituted or unsubstituted heteroalkyl; and n is an integer from 3 to 30.

13. The method according to claim 12, wherein said ion exchange chromatographic moiety together with said first linker has the formula:

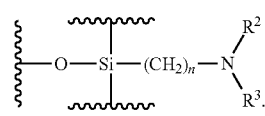

14. The method of claim 13, wherein said ion exchange chromatographic moiety together with said first linker has the formula:

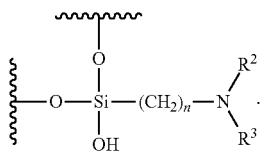

15. The method according to claim 8, wherein said urea hydrophilic interaction chromatography moiety together with said second linker has a formula which is:

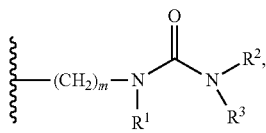

wherein $R^1$, $R^2$ and $R^3$ are independently selected from H, substituted or unsubstituted alkyl and substituted or unsubstituted heteroalkyl; and
m is an integer independently selected from 8 to 40.

16. The method according to claim 15, wherein said urea hydrophilic interaction chromatographic moiety together with said second linker has a formula which is:

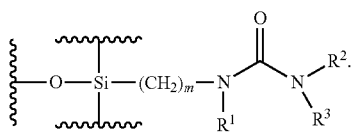

17. The method of claim 16, wherein said urea hydrophilic interaction chromatographic moiety together with said second linker has a formula which is:

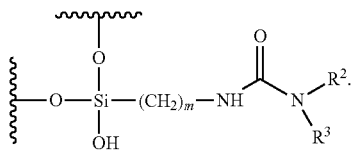

18. The method according to claim 5, wherein a member selected from said first substrate, said second substrate and a combination thereof is a silica substrate.

19. The method according to claim 5, wherein a member selected from said first substrate, said second substrate and a combination thereof is a particle.

20. The method according to claim 19, wherein a member selected from said first substrate, said second substrate and a combination thereof is a silica particle having a diameter of from about 1 μm to about 20 μm.

21. The method according to claim 1, wherein said electrolyte is present in an amount from about 1 mM to about 50 mM.

22. The method according to claim 21, wherein said organic solvent is present in said eluent in an amount up to about 95% (v/v) of said eluent.

23. The method according to claim 1, further comprising (b) prior to step (a), preparing a first precursor glycan mixture by treating a solution of at least one glycoprotein with a glycosidase, thereby forming said first precursor glycan mixture.

24. The method according to claim 23, wherein in said glycosidase is a member selected from PNGase F, PNGase A and a combination thereof.

25. The method according to claim 23, further comprising (c), following step (b), preparing a second precursor glycan mixture, comprising said first glycan component and said second glycan component, by a method comprising:
(i) precipitating proteins in said first precursor glycan mixture, forming a mixture comprising precipitated proteins and a supernatant;
(ii) pelleting said precipitated proteins by centrifuging said mixture of step (i), forming a two-phase mixture;
(iii) removing said supernatant from said two-phase mixture, forming an isolated supernatant; and
(iv) dialysing said isolated supernatant, thereby forming said second precursor glycan mixture; or
(i) submitting said first precursor glycan mixture to reverse phase high performance liquid chromatography, thereby forming said second precursor glycan mixture.

26. The method of claim 25, further comprising (d), following step (c), preparing a labeled glycan mixture comprising a labeled said first glycan component and labeled said second glycan component by a method comprising, submitting said second precursor glycan mixture to a mixture comprising a reactive, detectable label under conditions effective to label a glycan in said second precursor glycan mixture with said detectable label, thereby preparing said labeled glycan mixture.

27. The method of claim 26, wherein said detectable label is a fluorescent label.

28. The method of claim 27, wherein said conditions are effective for reductive amination by said detectable label of a reducing moiety of a member selected from said first glycan component, said second glycan component and a combination thereof, wherein said detectable label comprises a reactive amine moiety.

29. The method of claim 27, wherein said fluorescent label is an aromatic amine.

30. The method of claim 29, wherein said aromatic amine is a member selected from 2-aminobenzoic acid, 2-aminobenzamide, 2-aminopyridine, 8-aminonapthaline-1,3,6-trisulfonic acid, 2-aminoacridone, and 9-aminopyrene-1,3,6-trisulfonic acid.

31. The method of claim 25, further comprising, (d) following step (c), treating said second precursor glycan mixture with a member selected from sialidase A, sialidase B and a combination thereof, thereby preparing said glycan mixture.

32. The method of claim 31, further comprising, (e) following step (a), submitting said resultant separated first glycan component and said second glycan component to analysis by mass spectrometry.

33. The method of claim 26, further comprising, following step (a), submitting said labeled first glycan component and said labeled second glycan component to analysis by mass spectrometry.

34. The method of claim 1 wherein said separating results in a chromatogram in which said first glycan component and said second glycan component have retention times proportional to their charge, such that a third glycan having a charge identical to that of said first glycan component or said second glycan component will have a retention time grouped with the glycan component of identical charge.

35. The method according to claim 1, wherein said multimodal chromatographic medium comprises a first ion exchange binding site and a second ion exchange binding site, wherein said first ion exchange binding site is an anion exchange site, and said second ion exchange binding site is a cation exchange site.

36. The method according to claim 35, wherein said multimodal chromatographic medium is an electrostatically aggregated chromtographic medium, wherein said anion exchange site is on a first substrate and said cation exchange site on a second substrate different from the first substrate, and said second substrate are electrostatically aggregated to each other.

37. A multimodal chromatographic method of separating a first glycan component from a second glycan component of a glycan mixture, said method comprising:
(a) contacting said glycan mixture with a multimodal chromatographic medium comprising an ion exchange chromatographic moiety bound to a first substrate through a first linker, said ion exchange chromatographic moiety together with said first linker has a formula:

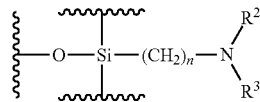

wherein
$R^2$ and $R^3$ are independently selected from H, substituted or unsubstituted alkyl and substituted or unsubstituted heteroalkyl; and
n is an integer from 3 to 30,
and an uncharged chromatographic moiety bound to a second substrate through a second linker, said uncharged chromatographic moiety selected from a reverse phase chromatographic moiety, a hydrophilic interaction chromatographic moiety and a combination thereof,
and an aqueous eluent comprising an electrolyte and an organic solvent under conditions effective to achieve said separating,
thereby separating said first glycan component and said second glycan component.

38. The method of claim 37, wherein said ion exchange chromatographic moiety together with said first linker has the formula:

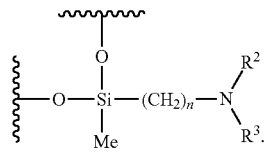

39. The method according to claim 37, wherein said first substrate and said second substrate are the same substrate.

40. A multimodal chromatographic method of separating a first glycan component from a second glycan component of a glycan mixture, said method comprising:
(a) contacting said glycan mixture with a multimodal chromatographic medium comprising an ion exchange chromatographic moiety bound to a first substrate through a first linker,
and an uncharged chromatographic moiety bound to a second substrate through a second linker, said uncharged chromatographic moiety together with said second linker has a formula selected from:

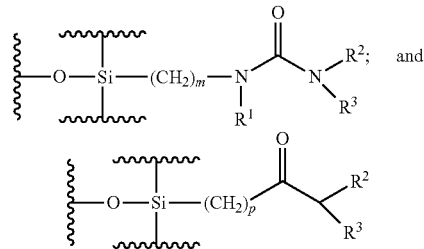

wherein
$R^1$, $R^2$ and $R^3$ are independently selected from H, substituted or unsubstituted alkyl and substituted or unsubstituted heteroalkyl; and
m and p are integers independently selected from 3 to 30,
and an aqueous eluent comprising an electrolyte and an organic solvent under conditions effective to achieve said separating,
thereby separating said first glycan component and said second glycan component.

41. A multimodal chromatographic method of separating a first glycan component from a second glycan component of a glycan mixture, said method comprising:
(a) preparing a first precursor glycan mixture by treating a solution of at least one glycoprotein with a glycosidase, thereby forming said first precursor glycan mixture;
(b) preparing a second precursor glycan mixture, comprising said first glycan component and said second glycan component, by a method comprising:
  (i) precipitating proteins in said first precursor glycan mixture, forming a mixture comprising precipitated proteins and a supernatant;
  (ii) pelleting said precipitated proteins by centrifuging said mixture of step (i), forming a two-phase mixture;
  (iii) removing said supernatant from said two-phase mixture, forming an isolated supernatant; and
  (iv) dialysing said isolated supernatant, thereby forming said second precursor glycan mixture; or
  (v) submitting said first precursor glycan mixture to reverse phase high performance liquid chromatography, thereby forming said second precursor glycan mixture;
(c) treating said second precursor glycan mixture with a member selected from sialidase A, sialidase B and a combination thereof, thereby preparing said glycan mixture; and
(d) contacting said glycan mixture with a multimodal chromatographic medium comprising an ion exchange chromatographic moiety bound to a first substrate and an uncharged chromatographic moiety bound to a second substrate, said uncharged chromatographic moiety selected from a reverse phase chromatographic moiety, a hydrophilic interaction chromatographic moiety and a combination thereof, and an aqueous eluent comprising an electrolyte and an organic solvent under conditions effective to achieve said separating, thereby separating said first glycan component and said second glycan component.

* * * * *